(12) United States Patent  
Ryan et al.

(10) Patent No.: US 8,694,334 B2
(45) Date of Patent: Apr. 8, 2014

(54) READMISSION RISK ASSESSMENT

(75) Inventors: Hugh H. Ryan, Lee's Summit, MO (US); Frank A. Azzaro, Olathe, KS (US); Pamela M. Baker, Olathe, KS (US); Chad Barrett Ruoff, Lee's Summit, MO (US); Donna J. Cappo, Centerview, MO (US)

(73) Assignee: Cerner Innovation, Inc., Kansas City, KS (US)

(*) Notice: Subject to any disclaimer, the term of this patent is extended or adjusted under 35 U.S.C. 154(b) by 164 days.

(21) Appl. No.: 13/284,088

(22) Filed: Oct. 28, 2011

(65) Prior Publication Data

US 2012/0046965 A1 Feb. 23, 2012

Related U.S. Application Data

(63) Continuation-in-part of application No. 12/817,602, filed on Jun. 17, 2010.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2, 3
See application file for complete search history.

(56) References Cited

U.S. PATENT DOCUMENTS

| 2005/0216312 | A1* | 9/2005 | Bellin et al. ....................... 705/3 |
| 2005/0222867 | A1 | 10/2005 | Underwood et al. |
| 2011/0246220 | A1 | 10/2011 | Albert |
| 2012/0004925 | A1* | 1/2012 | Braverman et al. ............... 705/2 |

OTHER PUBLICATIONS

Non Final Office Action of U.S. Appl. No. 12/817,602, Mailed Mar. 14, 2012, 16 pages.
Final Office Action of U.S. Appl. No. 12/817,602 mailed Oct. 24, 2012, 15 pages.
Notice of Allowance in U.S. Appl. No. 12/817,602, mailed Sep. 13, 2013, 25 pages.
Perez-Valdivieso, et al., "Cardiac-surgery associated acute kidney injury requiring renal replacement therapy. A Spanish retrospective case-cohort study", BMC Nephrology 2009, www.biomedcentral.com/1471-2369/10/27.
Justice, Amy C., et al. "Assessing the Generalizability of Prognostic Information", Ann Intern Med. 1999; 130:515-524., 1999 American College of Physicians-American Society of Internal Medicine.

* cited by examiner

*Primary Examiner* — Robert Morgan
*Assistant Examiner* — Maroun Kanaan
(74) *Attorney, Agent, or Firm* — Shook Hardy & Bacon LLP

(57) ABSTRACT

Readmission risk of patients admitted to a healthcare facility are determined using a generic readmission risk algorithm. The readmission risk assessment of patients may be based on portions of a patient's profile and may be performed before, during, and after their index admission. Based on the readmission risk assessment of patients, those patients that are at a greater risk for readmission may be identified. A readmission prevention worklist may be provide that identifies those patients and facilitates managing the risk of readmission for those patients.

18 Claims, 21 Drawing Sheets

| ORDERS | | | | | |
|---|---|---|---|---|---|
| POWERORDERS | | | | | |
| + ADD | ⚡ DOCUMENT MEDICATION BY HX | RECONCILIATION ▾ | | | | |
| ORDERS | MEDICATION LIST | DOCUMENT IN PLAN | | | | |
| ▶ PLANS | | | | | |
| ▾ ⊘ | + ADD TO PHASE ▾ ⚠ CHECK ALERTS | START: NOW ⏷ | DURATION: NONE ⏷ … | | |
| ▷ | COMPONENT | STATUS | DETAILS | | |
| ☐ | ✐ FEMTIN | | | | |
| ☐ | ✐ IRON LEVEL (FE LEVEL) | | | | |
| ☐ | ✐ MAGNESIUM LEVEL (MG LEVEL) | | | | |
| ☐ | ✐ PHOSPHORUS LEVEL | | | | |
| ☐ | ✐ IRON PERCENT SATURATION | | | | |
| ☐ | ✐ PTT (APTT) | | | | |
| ☐ | ✐ PT (PROTHROMBINE TIME) | | | | |
| ☐ | ✐ URINALYSIS MICROSCOPIC (UA MICROCOPIC) | | | | |
| ⊟ DIAGNOSTIC TESTS | | | | | |
| | ◈ CONSIDER ECHOCARDIOGRAPHY FOR EJECTION | | | | |
| ☐ | ✐ ELECTROCARDIOGRAM | | | | |
| ☐ | ✐ CARDIAC ECHO TRANSESOPHAGEAL | | | | |
| ☐ | ✐ CARDIAC ECHO TRANSTHORACIC | | | | |
| ☐ | ✐ XR CHEST 1 VIEW (CHEST XR 1 VIEW) | | | | |
| ☐ | ✐ XR CHEST 2 VIEWS (CHEST XR 2 VIEWS) | | | | |
| ⊟ SPECIAL | | | | | |
| | ◈ THIS PATIENT MEETS CRITERIA FOR "HIGH" 30 DAY READMISSION RISK. | | PLEASE INITIATE THE HEART FAILURE READMISSION RISK PROTOCOL. | | |
| ☑ | ▦ HEART FAILURE READMISSION RISK PROTOCOL | | | | |

| HEART FAILURE OUTPATIENT SURVEILLANCE | CALL | NO CALL | | | HIGH RISK INPATIENTS | |
|---|---|---|---|---|---|---|
| PATIENT NAME | AGE | PHONE # | DISCHARGE DAYS | LAST CONTACTED | FOLLOW-UP VISIT | VISIT COMPLETE? |
| + ADAMS, JOHN | 45 | 816-555-1234 | 1 | N/A | THUR 01/28 | N/A |
| + ARTHUR, CHESTER | 61 | 816-555-1235 | 30 | FRI 01/02 | WED 12/30 | YES |
| + BUCHANAN, JAMES | 48 | 816-555-1236 | 5 | FRI 01/22 | MON 01/25 | ? |
| + BUSH, GEORGE | 55 | 816-555-1237 | 14 | WED 01/20 | MON 01/18 | YES |
| + CARTER, JIMMY | 60 | 816-555-1238 | 12 | MON 01/25 | TUES 01/19 | NO |
| + CLEVELAND, GROVER | 55 | 816-555-1239 | 10 | FRI 01/22 | WED 01/20 | YES |
| + PATIENT, JOE | 55 | 816-555-1240 | 10 | FRI 01/22 | THRU 01/21 | YES |

*FIG. 6.*

READMISSION RISK SUMMARY

PATIENT, JOE M/43 YEARS DOB: 12/09/1965 PRIMARY CARE PHYSICIAN: PHYSICIAN, JOE

THIS PAGE IS NOT A COMPLETE SOURCE OF VISIT INFORMATION.

| HISTORY | |
|---|---|
| NYHA CLASS: | II |
| EJECTION FRACTION: | 35% 10/11/09 |
| READMISSION RISK SCORE: | 44% |
| LIFESTYLE FACTORS: | SMOKING, A... |
| LAST CONTACT: | FRI, JAN 22 09 |
| BASELINE WEIGHT: | 205 LBS. |

DISCHARGE DATA: JANUARY 15

— NORMAL WEIGHT NET = 9LBS
···· NORMAL WEIGHT NET = 9LBS

| SURVEILLANCE +ADD | | - |
|---|---|---|
| | MON 01/18 | WED 01/20 |
| SHORTNESS OF BREATH | WITH ACTIVITY | WHILE RECLINE |
| SIGNS/SYMPTOMS | FATIGUE | FATIGUE |
| HOME OXYGEN | PRN | PRN |
| ENERGY LEVEL | 1 = LOW | 3 = MODERATE |
| BLOOD PRESSURE | 118/74 | 135/78 |
| WEIGHT | 205 LBS | 206 LBS |
| WALKING TIME | 10 MIN | 15 MIN |
| PLAN OF ACTION | NONE | PCP VISIT |

| HOME MEDICATIONS (7 ACTIVE) | - |
|---|---|
| ASPIRIN 81MG 1 TAB(S), BY MOUTH, DAILY | |
| KCl 20MEQ 1 TAB(S), BY MOUTH, TWICE DAILY | |
| LASIX 40MG 1 TAB(S), BY MOUTH, TWICE DAILY | |
| METFORMIN 500MG 1 TAB(S), BY MOUTH, TWICE DAILY | |
| METOPROLOL 25MG 1 TAB(S), BY MOUTH, TWICE DAILY | |
| OMEGA-3 POLYUNSATURATED FATTY ACIDS 3 CAPSU... | |
| XANEX 0.25MG 1TAB(S), BY MOUTH, AS NEEDED... | |

| PROBLEMS (4 ACTIVE) | - |
|---|---|
| CORONARY ARTERY DISEASE (414.10) | |
| DIABETES (249) | |
| HEART FAILURE (428.9) | |
| HYPERTENSION (410) | |

| SIGNIFICANT EVENTS (1) | - |
|---|---|
| HEART FAILURE: HIGH RISK | |
| # OF ADMISSIONS | |
| 30 DAYS = 0 | |
| 60 DAYS = 1 | |
| 90 DAYS = 2 | |
| 1 YEAR = 4 | |

| DOCUMENTS (2) | AUTHOR | DATE |
|---|---|---|
| DISCHARGE NOTE | PHY, JOE | 12/9 |
| CARDIOLOGY NOTE | PHY, JOE | 12/9 |

*FIG. 7.*

HEART FAILURE OUTPATIENT SURVEILLANCE – PATIENT, JOE
*PERFORMED ON: 01/26/2010  1131  CST

COMMUNICATION

SIGNS AND SYMPTOMS
- ☐ NONE    ☐ ORTHOPNEA
- ☐ COUGH   ☐ PALPITATIONS
- ☐ EDEMA   ☐ PAROXYSMAL NOCTUR
- ☐ FATIGUE ☐ SYNCOPE

SIGNS AND SYMPTOMS
- ○ SHORTNESS OF BREATH AT REST
- ○ SHORTNESS OF BREATH AT REST RECLINING
- ○ SHORTNESS OF BREATH AT SITTING UP
- ○ SHORTNESS OF BREATH WITH ACTIVITY
- ○ SHORTNESS OF BREATH AFTER RECLINING AT NIGHT

DATE CONTACTED: //****

OXYGEN FLOW RATE AT REST    L/MIN
OXYGEN FLOW RATE WITH ACTIVITY    L/MIN

ENERGY LEVEL
○ 1 = LOW
○ 2
○ 3 = MODERATE
○ 4
○ 5 = NORMAL

WEIGHT    KG

SYSTOLIC BP  MMHG  / DIASTOLIC BP  MMHG

WALKING TIME  MINUTE(S)

PLAN OF ACTION
☐ NONE                ☐ CALL PRIMARY CARE PHYSICIAN
☐ CALL CARDIOLOGIST   ☐ GO TO EMERGENCY DEPARTMENT
☐ CALL CLINIC

SURVEILLANCE COMPLETE
○ YES
○ NO

NOTES

DATE OF NEXT CONTACT: //****

READMISSION PREVENTIONIST WORKLIST    SHOW LEGEND THIS PAGE IS NOT A COMPLETE SOURCE OF VISIT INFORMATION
SELECT LIST: -SELECT LIST-▼  CUSTOMIZE PATIENT LIST->  ♣MOVE TO LIST

| INPATIENT | DISCHARGED | PRE-ADMISSION | | | | | |
|---|---|---|---|---|---|---|---|
| PATIENT INFORMATION▼ | ADMIT DIAGNOSIS | SUPPORT SERVICES | PLAN OF CARE | DISPOSITION | FOLLOW UP | NOTES |
| ⓘ BENTLY, JAMES O., 49YO M | HEART FAILURE | ✓CASE MANAGEMENT | ○READMISSION POWERPLAN | ✗NOT DOCUMENTED | ✗ | 📝 |
| 30 DAY READMISSION HYPERTENSION | | | | | | |
| D/C: 07/17/2011  ADMIT/LOS: 07/07/11 10D | STROKE | ✗SOCIAL SERVICE ✓HOME HEALTH ✗PT | ○READMISSION POWERPLAN | ✗NOT DOCUMENTED | ✗ | 📝 |
| FIN: 809000123  ADMITTING: DR. RYAN | | | | | | |
| ▸△ WILLARD, SAM, 40YO M | APPENDICITIS | ✓NONE NEEDED | ○READMISSION POWERPLAN | ✓HOME | ✓ | 📝 |
| LOC: 4N:123-1  ADMIT/LOS: 02/17/11 5D | | | | | | |
| FIN: 2235567  ADMITTING: DR. HOWARD | | | | | | |
| ▸△ SRINIVASAN, RAHUL, 18YO M | HEART FAILURE | ✗SOCIAL SERVICES | ○READMISSION POWERPLAN | ✓HOME W/DAUGHTER | ✗ | 📝 |
| LOC: 4N:213-1  ADMIT/LOS: 02/02/11 4D | | | | | | |
| FIN: 8022123  ADMITTING: DR. HUBER | | | | | | |

| READMISSION PREVENTIONIST WORKLIST | | SHOW LEGEND THIS PAGE IS NOT A COMPLETE SOURCE OF VISIT INFORMATION | | | |
|---|---|---|---|---|---|
| SELECT LIST: [SELECT LIST ▼] CUSTOMIZE PATIENT LIST-> ⇄ MOVE TO LIST | | | | | |
| [INPATIENT] [DISCHARGED] [PRE-ADMISSION ▼] | | | | | |
| PATIENT INFORMATION ▼ | D/C DIAGNOSIS | SUPPORT SERVICES | DISPOSITION | FOLLOW UP | NOTES |
| ▸△ BENTLY, JAMES O., 49YO M 🗎<br>D/C: 07/17/2011  ADMIT/LOS: 07/07/11 10D<br>FIN: 00877321  ADMITTING: DR. RYAN | EXACERBATION OF DIASTOLIC HF | ✓CARE MANAGEMENT<br>✓HOME HEALTH | ✓HOME W/ HOME HEALTH | 08/22/11 | 🗎 |
| ▸△ ASHTON, BARBARA, 93YO F 🗎<br>D/C: 07/17/2011  ADMIT/LOS: 07/07/11 10D<br>FIN: 80900123  ADMITTING: DR. RYAN | STROKE | ✓HOME HEALTH<br>✓OT<br>✓PT | ✓HOME W/DAUGHTER | 08/22/11 | 🗎 |
| ▸△ WILLARD, SAM, 40YO M 🗎<br>LOC: 4N:123-1  ADMIT/LOS: 02/17/11 5D<br>FIN: 2235567  ADMITTING: DR. HOWARD | APPENDICITIS | ✓NONE NEEDED | ✓HOME | 📅 08/14/11 | 🗎 |
| ▸△ SRINIVASAN, RAHUL, 18YO M 🗎<br>LOC: 4N:213-1  ADMIT/LOS: 02/02/11 4D<br>FIN: 8022123  ADMITTING: DR. HUBER | HEART FAILURE | ✓SOCIAL SERVICES | ✓HOME | 08/14/11 | 🗎 |

READMISSION RISK ASSESSMENT

CROSS-REFERENCE TO RELATED APPLICATIONS

This application is a continuation-in-part of U.S. patent application Ser. No. 12/817,602, filed Jun. 17, 2010, which is herein incorporated by reference in its entirety.

BACKGROUND

An unplanned readmission occurs when a patient is readmitted to a hospital within a certain period of time (e.g., 30 days) after having been discharged from the hospital for treatment of the same or related condition. Readmission rates are particularly high with certain conditions, such as heart failure and pneumonia. Hospitals are typically concerned with reducing the number of unplanned readmissions as they may reflect upon the quality of treatment provided by the hospitals and also result in significantly increased costs. Often, readmissions may have been preventable if the patients received proper care while admitted at the hospitals during the first visit and/or if the patients' length of stay had been extended. Additionally, readmissions may have been preventable if proper monitoring and education had been provided to patients after discharge. However, it is typically difficult to identify the proper inpatient treatments and post-discharge care appropriate for properly treating patients and preventing readmissions.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention generally relate to assessing the readmission risk of patients admitted to a healthcare facility using a generic readmission risk algorithm. The readmission risk assessment of patients may be based on portions of a patient's profile and may be performed before, during, and after their index admission. Based on the readmission risk assessment of patients, those patients that are at a greater risk for readmission may be identified. A readmission prevention worklist may be provide that identifies those patients and facilitates managing the risk of readmission for those patients.

Accordingly, in one aspect, an embodiment of the present invention is directed to one or more computer storage media storing computer-useable instructions that, when used by one or more computing devices, cause the one or more computing devices to perform a method. The method includes applying a readmission risk algorithm for each patient admitted to a healthcare facility. The method also includes responsive to applying the readmission risk algorithm to each patient admitted to the healthcare facility, identifying a subset of patients at risk for readmission. The method further includes generating a user interface to manage the subset of patients at risk for readmission. The method still further includes providing the user interface for presentation to a clinician.

In another embodiment, an aspect of the invention is directed to one or more computer storage media storing computer-useable instructions that, when used by one or more computing devices, cause the one or more computing devices to perform a method. The method includes accessing patient information for a patient at a healthcare facility and determining a risk for readmission for the patient based on the patient information and a readmission risk algorithm that is generic to patients admitted by the healthcare facility. The method also includes identifying the patient as being at risk for readmission based on the patient information and the readmission risk algorithm. The method further includes adding the patient to a subset of patients identified as being at risk for readmission. The method still further includes providing a user interface for presentation that identifies at least a portion of the subset of patients identified as being at risk for readmission.

A further embodiment of the present invention is directed to one or more computer storage media storing computer-useable instructions that, when used by one or more computing devices, cause the one or more computing devices to perform a method. The method includes accessing patient information for a first patient admitted or planned to be admitted to a healthcare facility. The method also includes determining, based on the patient information, if each of a first set of risk factors is satisfied. The first set of risk factors includes: the first patient is being admitted within 30 days from a previous admission, the first patient is diagnosed with one of a plurality of predetermined conditions, the first patient's age is above a threshold age and the patient lives in social isolation, and the first patient has a length of stay at the healthcare facility greater than a threshold length of stay. The method also includes determining, based on the patient information, if each of a second set of risk factors is satisfied. The second set of risk factors includes: a number of emergency department visits for the first patient over a given time period exceeds a threshold number of emergency department visits, a number of admissions for the first patient over a given time period exceeds a threshold number of admissions, a comorbidity score for the first patient exceeds a comorbidity score threshold, the first patient has a predetermined type of insurance, and the first patient is being admitted to the intensive care unit. The method further includes identifying the first patient as being at risk for readmission based on at least one risk factor from the first set of risk factors being satisfied or based on at least two risk factors from the second set of risk factors being satisfied. The method still further includes providing a user interface for presentation that facilitates managing a plurality of patients identified as being at risk for readmission, the plurality of patients including the first patient.

BRIEF DESCRIPTION OF THE DRAWINGS

The present invention is described in detail below with reference to the attached drawing figures, wherein:

FIG. 5 is a screen display of an exemplary view illustrating a user interface for generating orders for patients including a initiating a readmission risk protocol in accordance with an embodiment of the present invention;

FIG. 6 is a screen display of an exemplary view illustrating an outpatient surveillance call list in accordance with an embodiment of the present invention;

FIG. 7 is a screen display of an exemplary view illustrating patient summary information for managing an outpatient call in accordance with an embodiment of the present invention;

FIG. 8 is a screen display of an exemplary view illustrating a user interface for tracking outpatient information in accordance with an embodiment of the present invention;

FIGS. 14A-F are screen displays of an exemplary readmission prevention worklist in accordance with an embodiment of the present invention.

DETAILED DESCRIPTION

Figure 1:
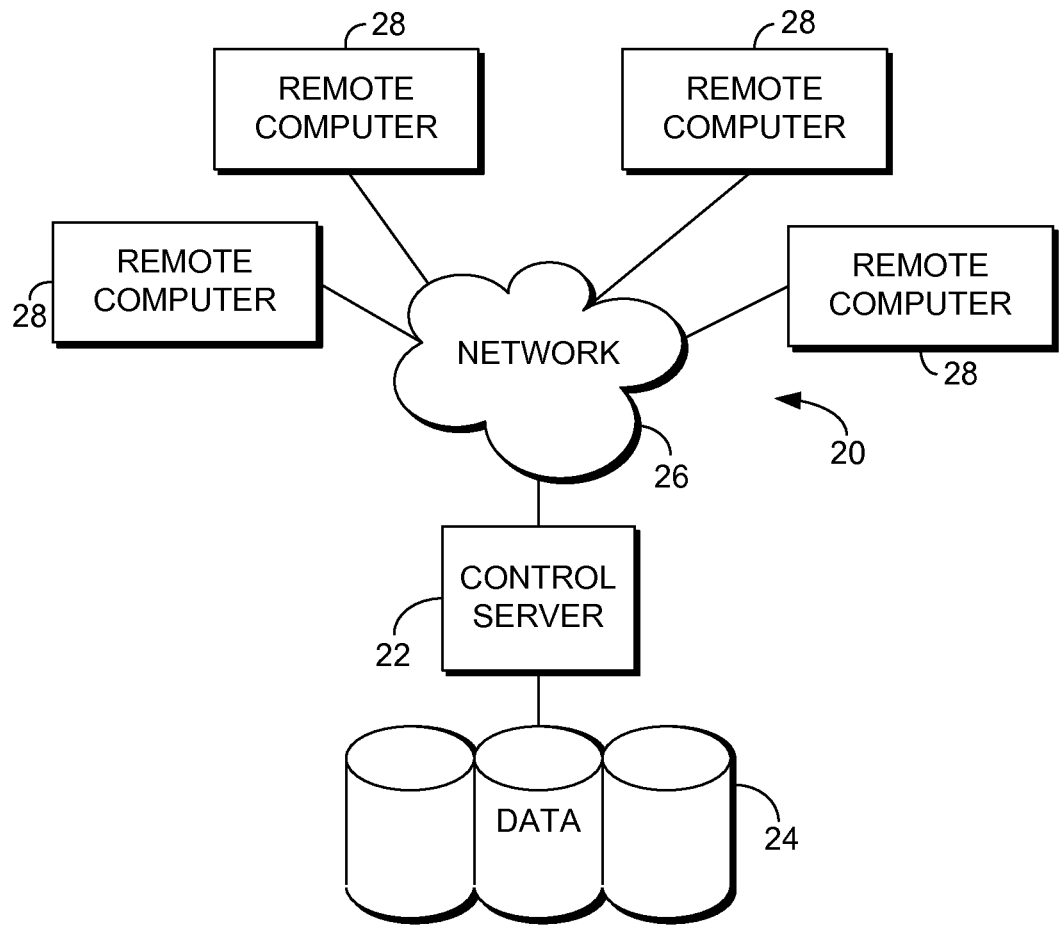
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods and systems for generating readmission risk prediction models using linear regression techniques. Embodiments of the present invention further provide computerized methods and systems for employing the readmission risk prediction models to assess the readmission risk of patients and determine inpatient treatment interventions and outpatient activities based on the patients' readmission risk.

Further embodiments are directed to applying a generic readmission risk algorithm to all patients admitted to a healthcare facility regardless of the patients' conditions to identify those patients at greater risk for readmission and providing a readmission prevention worklist to manage those patients.

An exemplary operating environment is described below. Referring to the drawings in general, and initially to FIG. 1 in particular, an exemplary medical computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Condition-Specific Readmission Risk

As previously mentioned, some embodiments of the present invention relate to generating readmission risk prediction models and using the readmission risk prediction models to facilitate inpatient treatment and/or outpatient activities. In embodiments, readmission risk prediction models may be generated utilizing logistic regression of existing clinically relevant data. Each readmission risk prediction model may be generated for a given condition using clinically relevant data from patients diagnosed with that condition. Additionally, in some embodiments, a readmission risk prediction model may be built around multiple conditions.

The readmission risk prediction models may be embedded within electronic medical systems or provided as a standalone software tool that facilitates determining the readmission risk of patients. In accordance with embodiments of the present invention, when a patient is admitted to a hospital or other clinical facility, the patient's condition may be diagnosed. Based on the patient's condition, a readmission risk prediction model may be selected and used to calculate a readmission risk score that represents the probability of readmission for the patient. The readmission risk may be based on readmission within a predetermined period of time, such as within 7 days after discharge, within 30 days after discharge, within 60 days after discharge, within 90 days after discharge, etc.

The readmission risk determined for patients may be utilized during hospitalization to drive clinical workflows for the patients. This may include linking the readmission risk for patients to clinical decision support and providing user interfaces to assist in identifying interventions for patients and also linking to orders to allow clinicians to enter orders based on review of readmission risk. For instance, readmission risk scores may help identify high readmission risk patients such that clinicians may determine proper interventions for those patients. In some embodiments, the system may recommend treatment interventions based on patients' readmission risks. For instance, readmission risk may be used to modify a patient's care plan including recommending alternate therapies, performing additional studies, and/or extending the patient's length of stay. Additionally, the readmission risk may be linked to clinical decision support and/or order subsystems such that clinicians may be identify and implement patient treatments deemed appropriate based in part on patients' readmission risks. In some embodiments, readmission risk scores may be recalculated over the length of hospitalization for patients and the patient care plans modified based on the recalculated readmission risk scores.

In addition to facilitating inpatient treatment, readmission risk may be used to facilitate discharge planning and outpatient activities. For instance, readmission risk may be used to determine the need for and scheduling of surveillance calls to patients and/or in-person appointments, in-home treatment, and patient education. In some embodiments, readmission risk scores may also be calculated after a patient has been discharged. Such post-discharge readmission risk scores may be used to modify outpatient activities and may warrant readmitting patients in some instances.

Figure 2:
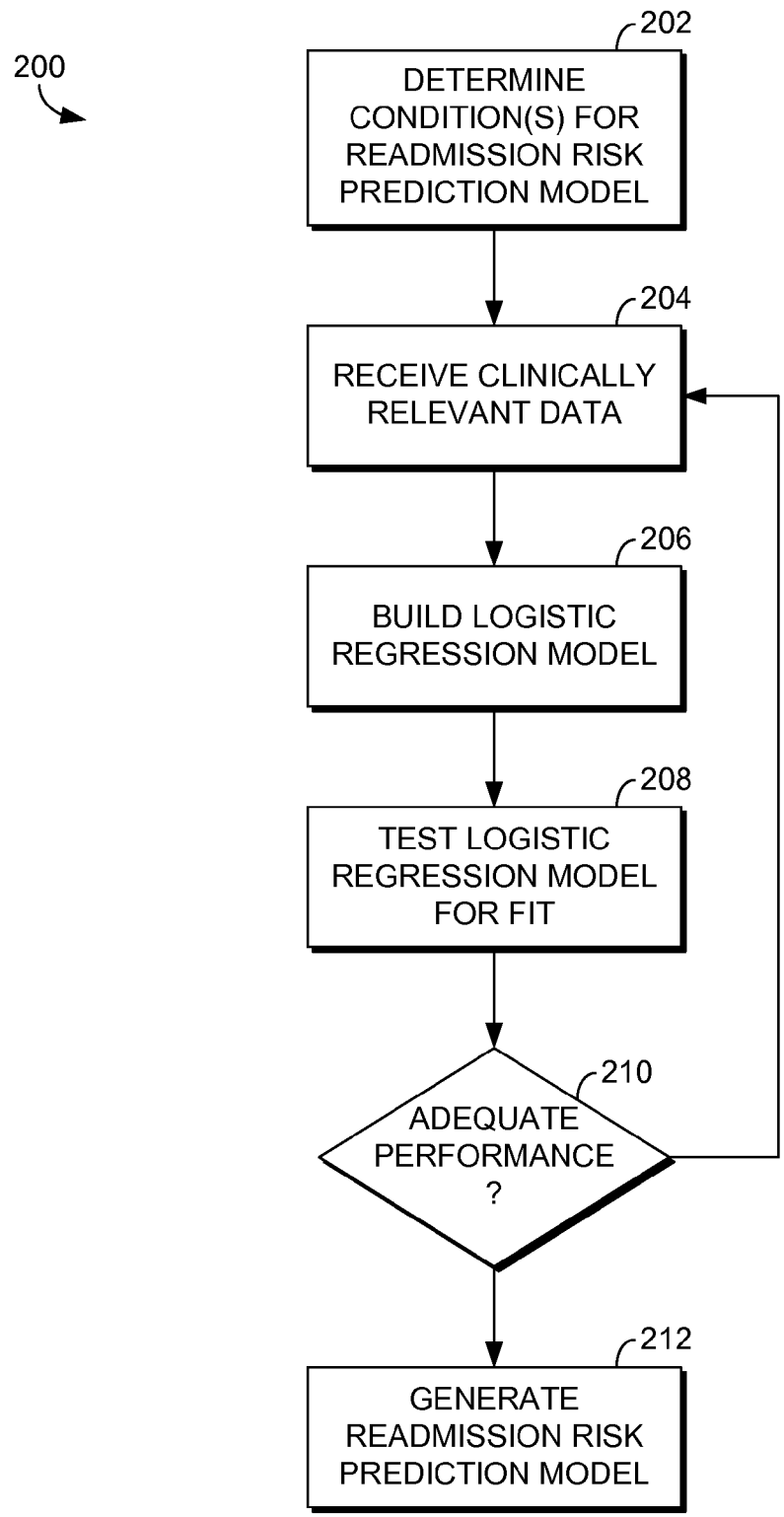
FIG. 2 is a flow diagram showing a method for generating a readmission risk prediction model in accordance with an embodiment of the present invention.

Referring now to FIG. 2, a flow diagram is provided that illustrates a method 200 for generating a readmission risk prediction model in accordance with an embodiment of the present invention. Initially, the condition around which the readmission risk prediction model will be generated is determined, as shown at block 202. As indicated previously, risk prediction models may be built around any given condition. For instance, a risk prediction model may be built around heart failure, acute myocardial infarction, pneumonia, acute kidney injury, sepsis, to name a few. In some embodiments, a readmission risk prediction model may be built around multiple conditions, each of which is identified at block 202.

Clinically relevant data for the identified condition is accessed at block 204 for use as training data. The clinically relevant data may come from any of a variety of public or private sources, including, for instance, hospital electronic medical records, research facilities, and academic institutions. The data may be collected manually or may be retrieved using electronic data gathering mechanisms. In embodiments, the process may include identifying relevant cases useful for constructing a readmission risk prediction model for the condition identified at block 202. Additionally, the process may include identifying input and output variables relevant to the identified condition. In some embodiments, evidence-based practices may be used in determining relevant cases and variables.

As shown at block 206, a logistic regression model is built using the retrieved clinically relevant data. In embodiments, the logistic regression model may be built around patient readmissions within one or more given time periods, such as readmission within 7 days after discharge, within 30 days after discharge, within 60 days after discharge, within 90 days after discharge, etc. The logistic regression model is then tested for model fit, as shown at block 208. This may include performing analyses to determine how well the model predicts outcomes, how well the model calibrates, and whether the model is clinically useful. By way of example only, the model may be tested by performing a receiver-operating characteristic (ROC) area-under-the-curve (C-statistic) analysis to determine how well the model predicts outcomes. As another example, the model may be analyzed using a chi-square test to determine how well the model calibrates.

Whether the performance of the logistic regression model is adequate based on the model testing is determined at block 210. If the performance of the logistic regression model is deemed to be inadequate, the process of selecting clinically relevant data and/or building a logistic regression model may be iterated until sufficient performance is achieved. A readmission risk prediction model is then generated using the output from the logistic regression model, as shown at block 212.

Figure 3A:
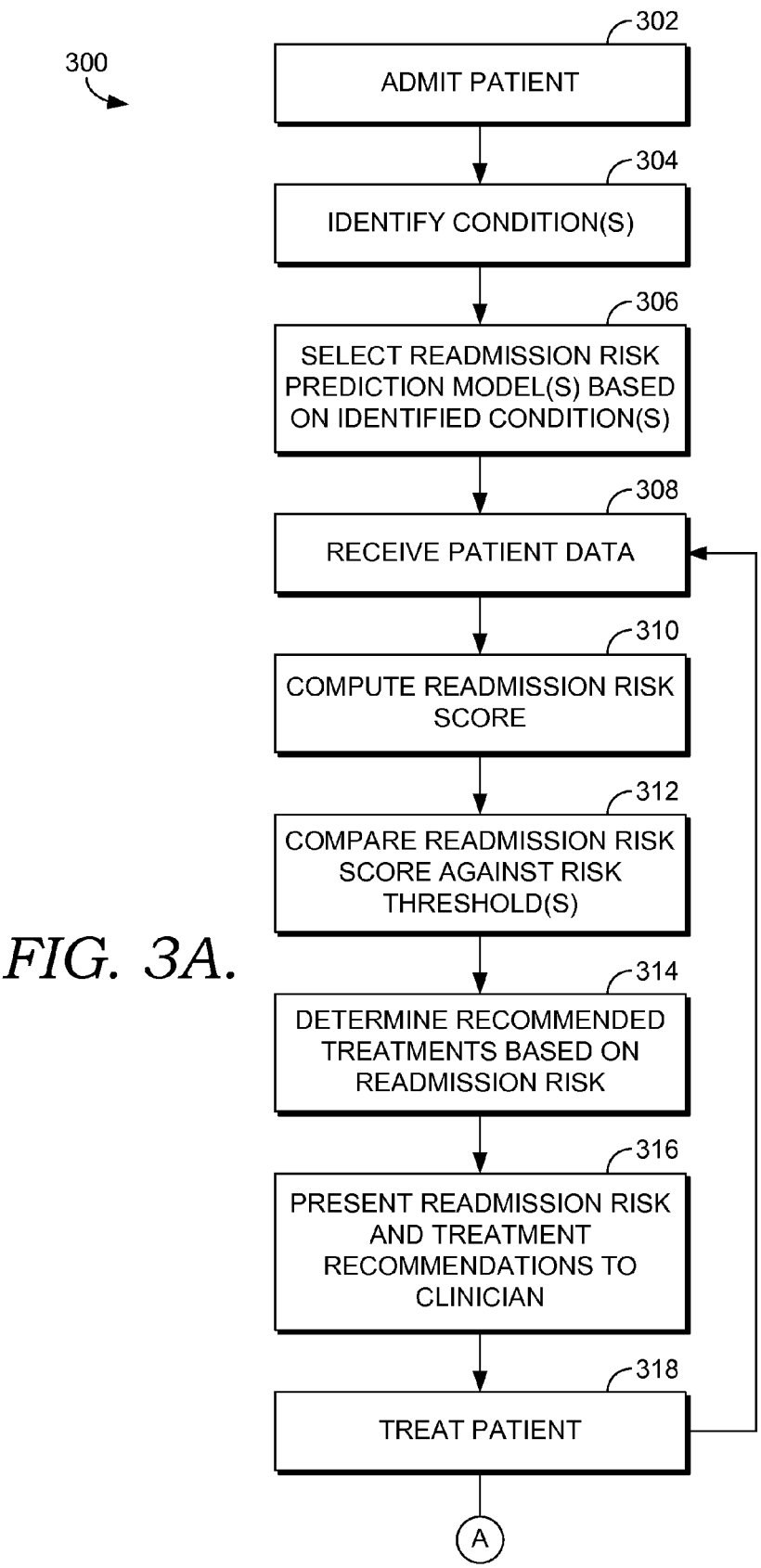
FIGS. 3A and 3B include a flow diagram showing a method for using readmission risk for inpatient treatment and outpatient activity planning in accordance with an embodiment of the present invention.
Figure 3B:
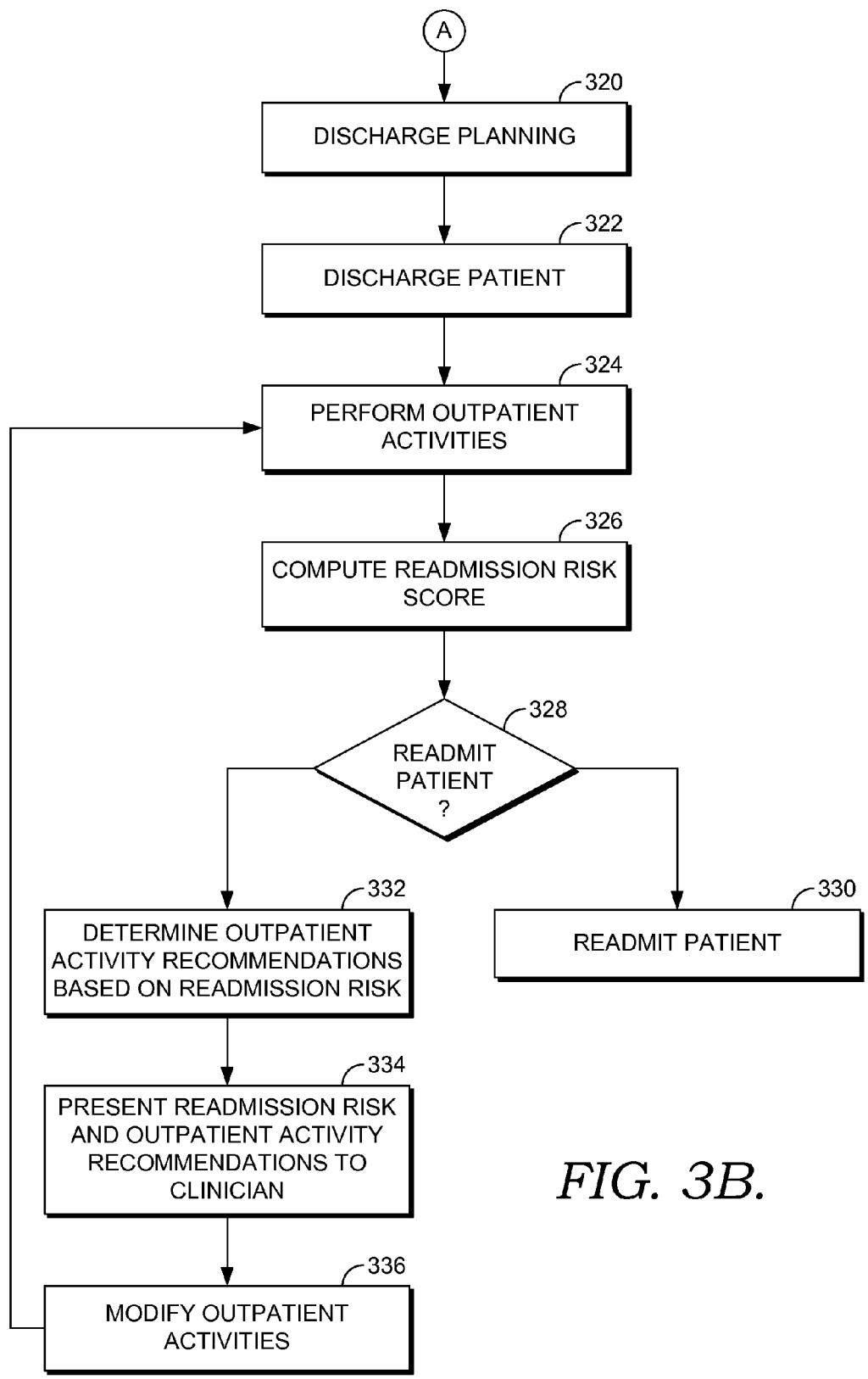

Turning next to FIGS. 3A and 3B, a flow diagram is provided that illustrates a method 300 for using a readmission risk score to facilitate treatment of a patient in accordance with an embodiment of the present invention. Initially, as shown at block 302, a patient is admitted to a hospital or other clinical facility. Upon admitting the patient, a condition is identified for the patient, as shown at block 304. In some instances, the patient may be suffering from a single condition and the single condition is identified, while in other instances, the patient may be suffering from multiple conditions and the multiple conditions are identified at block 304.

A readmission risk prediction model is selected at block 306 based on the condition identified for the patient at block 304. In instances in which a single condition is identified, a readmission risk prediction model corresponding with that condition is selected. For instance, if the patient is identified as suffering from heart failure, the system selects a readmission risk prediction model that was built around heart failure patients to determine the readmission risk of heart failure patients. In some embodiment in which multiple conditions are identified for the patient, a single readmission risk prediction model built around those identified conditions is selected. For instance, a patient may be suffering from heart failure and pneumonia, and a single readmission risk prediction model built around those two conditions may be selected. In other embodiments in which multiple conditions are identified, multiple readmission risk prediction models are selected, each model corresponding with one of the identified conditions. For instance, if the patient is suffering from heart failure and pneumonia, a readmission risk prediction model for heart failure and a readmission risk prediction model for pneumonia may both be selected and used in conjunction to identify readmission risk for the patient.

Patient data for the patient is received at block 308. The patient data may include demographic data and/or clinically relevant data for the patient. Additionally, the data received at block 308 may be dependent upon the selected readmission risk prediction model. In particular, each readmission risk prediction model may have a number of input variables that are relevant to that model. As such, data corresponding with the relevant variables are received as input to the model for readmission risk assessment purposes.

In some embodiments, the readmission risk prediction models may be embedded within an electronic medical system that includes electronic medical records or otherwise may be in communication with electronic medical records for patients. In such embodiments, the patient data may be received by accessing the electronic medical record for the patient and retrieving the relevant data. In some instances, patient data used by the readmission risk prediction model may not be available in the patient's electronic medical records, and the system may prompt a clinician to enter the data or to order particular tests to be performed to obtain the data. In further embodiments, the readmission risk prediction models may be provided in standalone software separate from an electronic medical record, and a clinician may enter the patient data as variables for the readmission risk prediction model. Any and all variations are contemplated to be within the scope of embodiments of the present invention.

A readmission risk score is computed using the selected readmission risk prediction model and the received patient data, as shown at block 310. The readmission risk score is then compared against one or more thresholds, as shown at block 312. In accordance with embodiments of the present invention, thresholds may be set by the clinical facility treating the patient, an external policy maker, and/or other entity and used to trigger treatment recommendations based on the risk of readmission. The thresholds may be condition-specific. For instance, a readmission risk threshold used for heart failure patients may differ from a readmission risk threshold used for pneumonia patients.

In some embodiments, a single threshold may be provided. If the readmission risk score exceeds the threshold, the patient is identified as a high risk for readmission. Alternatively, if the readmission risk score is below the threshold, the patient is considered to be a low readmission risk. In other embodiments, multiple thresholds may be set providing more than two ranges of readmission risk scores corresponding with more than two levels of readmission risk.

As shown at block 314, treatment recommendations are determined based on the patient's readmission risk level. The treatment recommendations may be any of a variety of different interventions intended to treat the patient's condition and reduce the likelihood that the patient would need to be readmitted. For instance, as noted above, a single threshold may be used such that the readmission risk score indicates either a low or high readmission risk. In some embodiments, if the readmission risk is low, no interventions may be recommended and the care plan may remain unmodified. Alternatively, if the threshold is exceeded such that the readmission risk is high, certain interventions or a modified care plan may be recommended based on the high readmission risk. In embodiments in which multiple thresholds are used providing multiple risk levels, treatment recommendations may be determined based on the risk level determined for the patient. In various embodiments of the present invention, the treatment recommendations may be predetermined for each risk level or the system may analyze or provide tools that allow a clinician to analyze the input variables used by the readmission risk prediction model to identify personalized treatment recommendations for the patient.

The readmission risk and/or recommended treatments for the patient are presented to a clinician, as shown at block 316. The readmission risk may be presented, for instance, as a readmission risk score comprising a percentage indicating the probability that the patient will need to be readmitted after discharge. In addition to or in lieu of presenting a readmission risk score, the readmission risk determined by comparison to one or more thresholds may be presented to a clinician. For example, the patient may be identified as a high readmission risk. As noted above, in some embodiments, the system may automatically recommended interventions based on the readmission risk level, and the system may present those interventions. In other embodiments, after determining that the readmission risk score exceeds certain thresholds, the system may provide tools to the clinician to allow the clinician to explore reasons why the readmission risk score is high and to determine the best treatment options for the patient.

In some embodiments, the readmission risk score and recommended treatments may only be presented if a threshold is exceeded by the patient's readmission risk score. For instance, if the patient's readmission risk score is low, no readmission risk information may be presented to the clinician and a routine care plan may be provided. In other embodiments, the system may provide an indication to the clinician that the readmission risk for the patient is low.

Treatment alternatives are selected, and the patient is treated, as shown at block 318. This may include performing a routine care plan if the readmission risk is low or performing a modified care plan including interventions recommended based on readmission risk exceeding certain thresholds. While the patient is treated, the readmission risk score may be recalculated as shown by the return to block 308. The readmission risk score may be recalculated at predetermined points in time or any time patient data is updated that may impact the readmission risk score for the patient. Based on the readmission risk score recalculations, different treatments options may be recommended and/or the patient's care plan may be modified. As such, the patient's readmission risk may be monitored during treatment and the patient's care modified as dictated by the patient's readmission risk.

In some embodiments, the system may monitor risk score trending for the patient during treatment and use such trending information to provide treatment recommendations. For instance, multiple readmission risk score calculations may indicate that the patient's readmission risk is decreasing, demonstrating that the current care plan is effective. Alternatively, readmission risk score trending may correspond with the patient's readmission risk remaining stable or even increasing, demonstrating that the current care plan is ineffective and/or that different interventions may be necessary.

After treating the patient, discharge planning is conducted prior to discharging the patient, as shown at block 320. This may include recalculating a readmission risk score for discharge planning purposes and/or using a previously obtained readmission risk score or risk score trending in discharge planning. In some embodiments, the patient's readmission risk score may be used to determine whether to discharge the patient. For instance, a rule may dictate that the patient may not be discharged until the patient's readmission risk score falls below a certain threshold or exhibits a certain downward trend over time.

Discharge planning may also include planning outpatient activities to be conducted after the patient is discharged. In embodiments, the patient's readmission risk score may be used in planning the outpatient activities for the patient. The outpatient activities may include performing patient monitoring, such as outpatient surveillance calls from a clinician to the patient, scheduling appointments for the patient, providing in-home healthcare, and educating the patient on healthcare issues related to the patient's condition. The patient's readmission risk score may be used to determine which outpatient activities to provide for the patient and may also determine a schedule for surveillance calls and/or appointments. For instance, if the patient is determined to be a high risk for readmission, the discharge planning may include placing the patient on a surveillance call list for high risk patients.

After discharge planning is performed, the patient is discharged, as shown at block 322. Any outpatient activities planned by the patient are performed after discharge, as shown at block 324. As noted above, the outpatient activities may include surveillance calls, appointments, as well as a number of other activities. Additionally, the patient's readmission risk score is calculated after the patient has been discharged, as shown at block 326. The readmission risk score may be calculated, for instance, based on additional information gathered from patient calls and appointments.

The readmission risk score calculated for a patient after discharge may be used for a number of purposes, such as determining whether to readmit the patient and whether to alter the patient's outpatient activities. Accordingly, as shown at block 328, a determination is made regarding whether to readmit the patient based on the readmission risk score calculated at block 326. This determination may be made, for instance, by comparing the readmission risk score to a threshold and determining to readmit based on the readmission risk score exceeding the threshold. The determination may also be made on readmission risk trending demonstrating a certain increase in readmission risk over time. The determination to readmit the patient may be based on clinician judgment as well. For instance, the system may present a notice to the clinician recommending that the patient be readmitted based on the readmission risk score and the clinician may review the notice and determine whether to readmit the patient. If it is determined that the patient should be readmitted, the patient may be readmitted as shown at block 330. If readmitted, the patient may be treated and the patient's readmission risk tracked and used for treatment purposes as described above.

Alternatively, it may be determined that the patient should not be readmitted at block 328. For instance, the patient's risk score may not exceed a predetermined threshold and/or a treating clinician may determine not to readmit. However, it may be desirable to modify the outpatient activities for the patient based on the readmission risk score. For instance, more frequent monitoring or additional testing may be desirable based on an elevated readmission risk score. As another example, no further outpatient activities may be deemed advisable based on a decreased readmission risk. Accordingly, as shown at block 332, outpatient activity recommendations are determined based on the outpatient readmission risk score. The readmission risk and/or outpatient activity recommendations are presented to a clinician, as shown at block 334. Based on the readmission risk and/or recommendations, the outpatient activities may be modified, as shown at block 336. The process of performing outpatient activities and recalculating readmission risk may be repeated until the patient is readmitted or until it is determined that outpatient activities and readmission risk score monitoring is no longer necessary.

As discussed previously, embodiments of the present invention include providing graphical user interfaces that facilitate inpatient treatment and outpatient activities based on readmission risk. FIGS. 4 through 8 are illustrative of user interfaces providing readmission risk information for patients and proving clinical decision support to clinicians based on readmission risk. It will be understood and appreciated by those of ordinary skill in the art that the screen displays of FIGS. 4 through 8 are provided by way of example only and are not intended to limit the scope of the present invention in any way.

Figure 4:
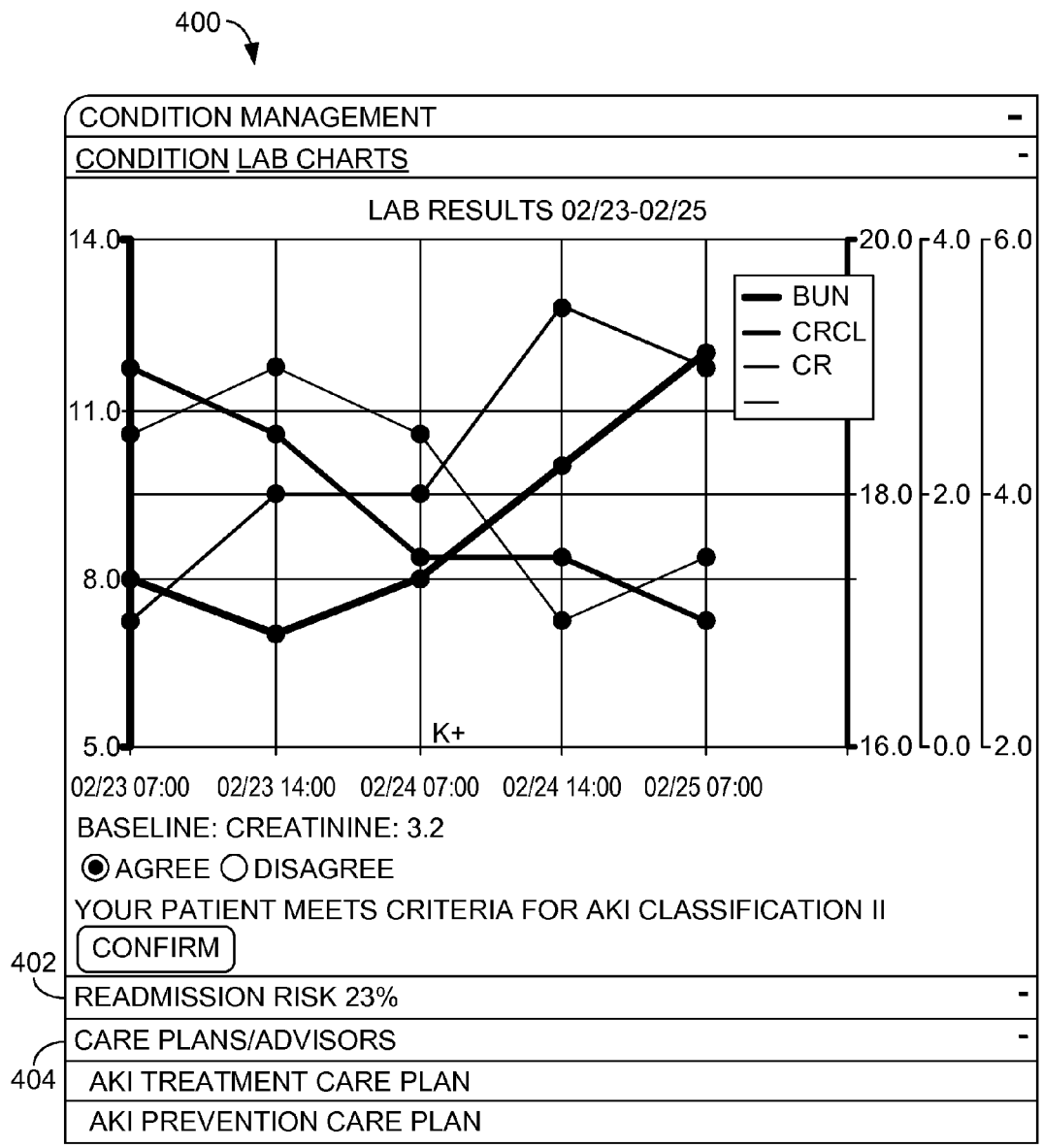
FIG. 4 is a screen display of an exemplary view illustrating condition management for a patient including lab results for the patient and the patient's readmission risk in accordance with an embodiment of the present invention.

Referring initially to FIG. 4, an illustrative screen display 400 is provided showing readmission risk in context of a condition management view for a patient in accordance with an embodiment of the present invention. The condition management view provides lab results information for the patient. Additionally, the condition management view provides an indication of readmission risk 402 for the patient. The condition management view further includes clinical decision support 404 in the form of care plans that are suggested by the system based on the patient's readmission risk. The clinician may review the information, including the patient's readmission risk, and determine whether to implement suggested care plans.

Turning to FIG. 5, an illustrative screen display 500 is provided that shows a user interface allowing a clinician to enter orders for a patient in accordance with an embodiment of the present invention. As shown in FIG. 5, the orders user interface allows the clinician to select from a number of different orders. The orders user interface also provides an indication: "This patient meets criteria for 'High' 30 day readmission risk" and suggests that the clinician initiate a heart failure readmission risk protocol. Accordingly, the clinician can review the information and understand that the patient has been identified as a high readmission risk. Based on this information, the clinician may select an order 502 to implement the heart failure readmission risk protocol for the patient.

As noted above, in addition to providing inpatient treatment tools, some embodiments of the present invention may provide tools facilitating outpatient activities for patients after discharge from a hospital. FIG. 6 provides an illustrative screen display 600 of an outpatient surveillance user interface in accordance with an embodiment of the present invention. The outpatient surveillance user interface may include two lists of patients: patients on a call list and patients on a no call list. A clinician may toggle between the two lists using the links 602 and 604. In some embodiments, patients having a high readmission risk may be placed on the call list while patients having a low readmission risk may be placed on the no call list. Patients may be moved from one list to another based on readmission risk and clinician judgment.

The screen display 600 illustrates a view of the patient call list. The list may be used to by clinicians to manage outpatient surveillance calls to patients. The list may include information such as contact information for each patient, how long ago each patient was discharged, when each patient was previously contacted, scheduled contact for each patient, etc.

In some embodiments, the clinician may access patient information by selecting a patient from the call list. For instance, FIG. 7 illustrates patient information when "Joe Patient" is selected from the call list. The patient summary includes a readmission risk score for the patient providing the clinician with an indication of the readmission risk for the patient. The patient summary also includes a variety of information that may be useful to a clinician responsible for contacting the patient, including surveillance information from previous contacts, medications, problems, and other related documentation. Embodiments of the present invention may further provide user interfaces for collecting patient information when performing outpatient surveillance. FIG. 8 provides an illustrate screen display 800 of such a user interface. The user interface and the information to be collected may be triggered based upon the readmission risk for the patient.

Non-Specific Readmission Risk Assessment and Surveillance

While previous embodiments are directed to determining readmission risk based on diagnosis of specific patient conditions, further embodiments of the present invention are directed to employing a generic readmission risk algorithm that may be applied to all patients for readmission prevention purposes. The condition-specific approaches discussed above apply to only those patients with specific conditions using sets of very specific clinical parameters that apply to particular patients diagnosed with specific conditions. In contrast, the currently-discussed embodiments are directed to readmission risk algorithms that may be applied to all patients (non-specific) in an attempt to assist in the process of readmission prevention. Essentially, the algorithm may be condition-agnostic as it may be run for patients regardless of the patients' conditions. As a result, these further embodiments are directed to efforts to accurately identify and stratify patients at increased risk for readmission regardless of the various patients' conditions. While patient conditions may be a factor used in an algorithm used in some embodiments, the algorithm is not employed solely for patients with those conditions but may be used for any patient regardless of patient condition.

By definition, all patients are readmission risks during their index admission. Embodiments of the present invention present algorithms that may be applied to all patients to provide an indication of an extent of readmission risk for the various patients. In some embodiments, an algorithm may be employed that provides a binary output that stratifies patients as a low or high risk level. Patients having a high risk level may be considered to be "at risk" for readmission. The algorithm may take into account clinical as well as social and situational information, and may be designed to fluctuate based on patient status and venue (i.e. upon scheduling, admission, daily, at follow up.) As a result, targeted analytics and workflow implications may be based on evaluation from the algorithm.

Portions of a patient's profile may be used to delineate and predict readmission risk. To do so, an algorithm may be employed that leverages clinical acumen, historical elements, and real-time data to predict and associate readmission risk levels for hospitalized patients before, during, and after their index admission. Multiple historical, clinical, and/or social elements may be queried and employed to assign a readmission risk level to patients. Assigning this level to patients will trigger actions and allow downstream processes to occur and notification to essential personnel of patients' risk for readmission in an effort to reduce the risk of hospital readmission. In some embodiments, the output of the result readmission prediction may be applied to a clinical process that will notify clinicians, providers, and the IT system of a patient's risk and may affect patient treatment, education, and other processes in an attempt to reduce the likelihood of readmission of patients.

Embodiments of the present invention logically define and structure elements commonly stored in a patient's medical record into a repeatable and reliable algorithm for readmission risk assessment. By way of example only and not limitation, the elements that may be employed include social, clinical and historical information, such as: patient condition; comorbidity; prior ED visits; prior admissions/readmissions; insurance status; acuity; social isolation; age; inpatient ICU length of stay; depression scoring; MDRO (MRSA) history; hospital acquired infection rates/surgical site infections; homelessness; BMI/nutrition status; seasonal trending/moon phases; education/employment level; long term infusion; psychiatric medications/history; multiple allergies; substance abuse; coagulopathy/warfarin therapy; residency (specifically jail inmate), hyper/hypoglycemic events (acute care/ambulatory/home care/post-acute care); falls (acute care/ambulatory/home care/post-acute care); pressure ulcers (acute care/ambulatory/home care/post-acute care); lab values (leukopenia, anemia values); renal function/acute kidney injury; oxygen dependency; specific procedures (such as radiology, oncology, surgical, orthopedic, vascular, etc.); race; and medication adherence issues. As these particular elements may by themselves make some sense to query for purposes of predicting readmission risk, combining any number of these high risk elements into a logical sequence can improve the sensitivity and specificity for defining readmission risk.

Figure 9:
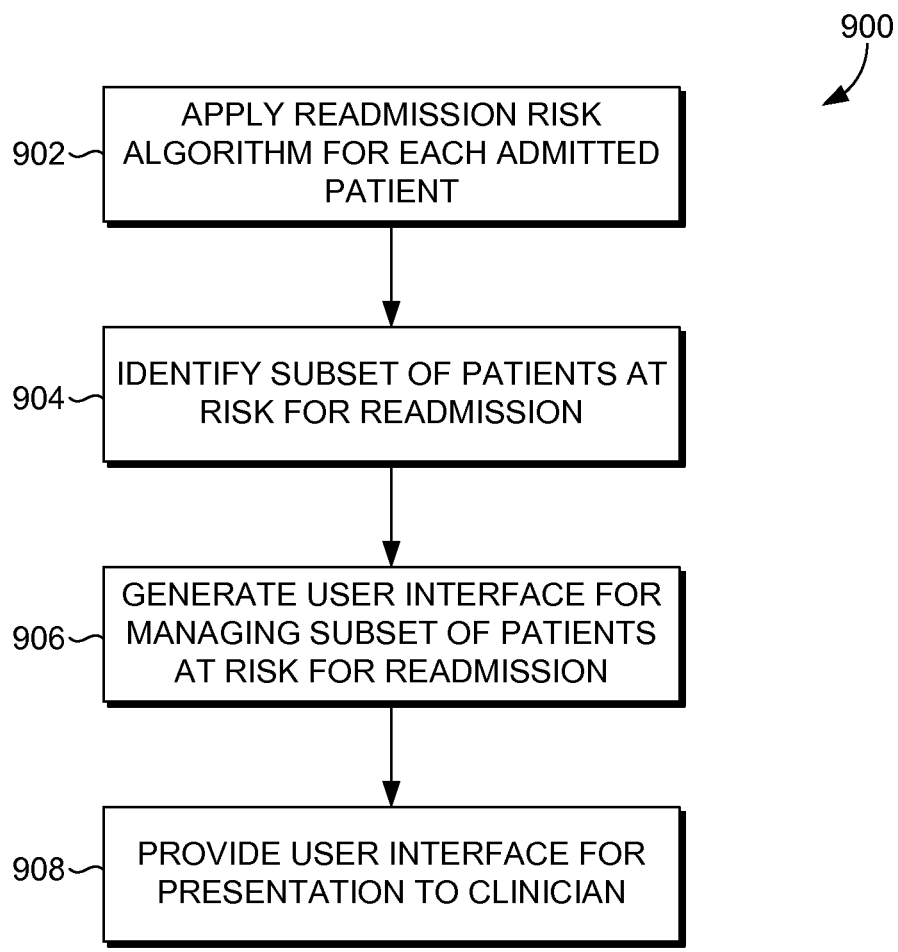
FIG. 9 is a flow diagram showing a method for assessing readmission risks of a population of patients in accordance with an embodiment of the present invention.

Turning now to FIG. 9, a flow diagram is provided that illustrates a method 900 for assessing readmission risks of a population of patients in accordance with an embodiment of the present invention. As shown at block 902, the method includes applying a readmission risk algorithm for each patient admitted to a healthcare facility. As noted above, the readmission risk algorithm may be an algorithm that may be applied generically across a patient population irrespective of patient conditions. The process may include accessing patient data for each patient for use by the readmission risk algorithm. Since the readmission risk algorithm may be applied across a patient population, the patient data accessed for each patient may be independent of any clinical conditions diagnosed for the patients.

In some embodiments, the readmission risk algorithm may be embedded within an electronic medical system that includes electronic medical records or otherwise may be in communication with electronic medical records for patients. In such embodiments, the patient data may be received by accessing the electronic medical record for the patient and retrieving the relevant data. In some instances, patient data used by the readmission risk algorithm may not be available in the patient's electronic medical records, and the system may prompt a clinician to enter the data or to order particular tests to be performed to obtain the data. In further embodiments, the readmission risk algorithm may be employed in standalone software separate from an electronic medical record, and a clinician may enter the patient data as variables for the readmission risk algorithm. Any and all variations are contemplated to be within the scope of embodiments of the present invention.

Based on the outcomes of the readmission risk algorithm, a subset of patients that are deemed to be at risk for readmission are identified, as shown at block 904. In some embodiments, the outcomes from applying the readmission risk algorithm may indicate each patient as either a high risk or a low risk. Those patients identified as a high risk would be considered as the patients at risk for readmission.

A user interface for managing patients at risk for readmission is generated, as shown at block 906. The user interface is provided for presentation to a clinician or other personnel, as shown at block 908. The user interface may consolidate the population of at-risk patients into a unified view, providing a number of advantages, including quality department assessment of at-risk patients and event tracking for follow-up appointments. The user interface may provide a view that allows easy assess for quality officials or other personnel to help standardize the care and enable prevention measures to avoid readmission, including driving workflows and improving efforts to prevent readmission. The user interface may complement readmission prevention efforts by consolidating valuable information, for instance, from within the healthcare facility's database, to present to the quality officials or other personnel. This information becomes knowledge that will help individuals to monitor key events which may lead to readmission, such as risk factors, care coordination, discharge planning, post-acute care, and follow-up compliance.

By providing such a user interface, embodiments may facilitate a readmission preventionist role within a healthcare facility. The readmission preventionist may be a person within a healthcare facility that oversees the readmission risk issues of patients. The user interface may provide a convenient view into at-risk patients to allow the readmission preventionist to, among other things, monitor at-risk patients, engage patient services (e.g., social service, case management, specialty services, home health, etc.), coordinate care, and monitor discharge processes and follow-up status. Ultimately, this supports an improved process for preventing hospital readmission.

Figure 10:
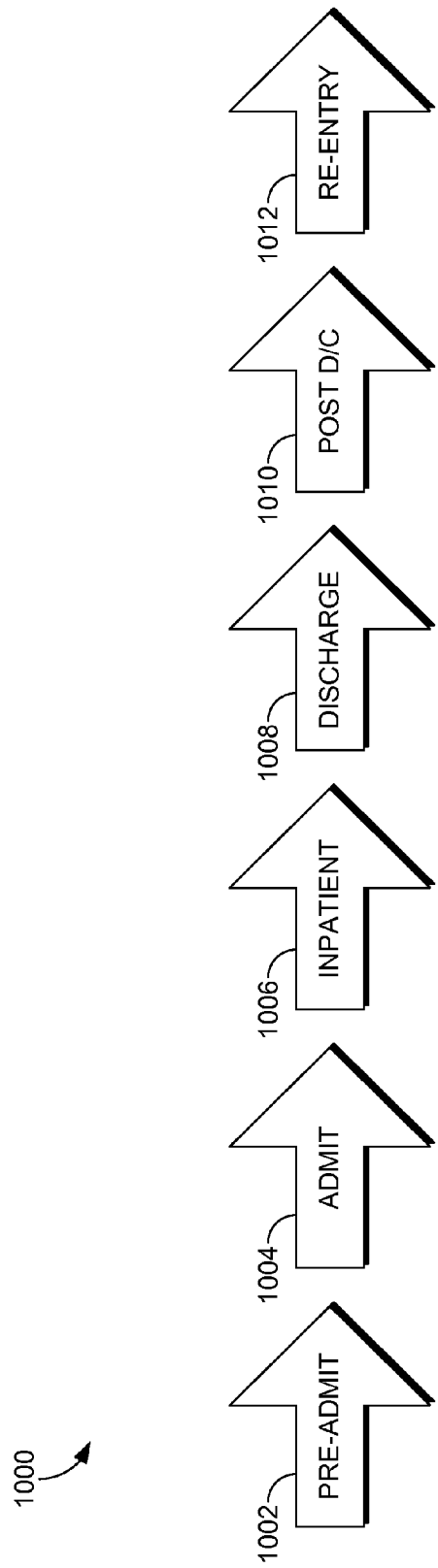
FIG. 10 is a diagram illustrating readmission risk algorithm and readmission prevention strategy may be applied for patients at different points throughout the care process in accordance with various embodiments of the present invention.

It should be noted that a readmission risk algorithm and readmission prevention strategy may be applied for patients throughout the care process. This is represented in FIG. 10, which illustrates performance of readmission risk assessment at a number of points in the care process, including pre-admission 1002, admission 1004, while an in-patient 1006, discharge 1008, post-discharge 1010, and re-entry 1012 (if the patient is readmitted). In some embodiments, the same readmission risk algorithm may be employed at the different points in time, while in other embodiments, different readmission risk algorithms may be employed at different points in time depending on factors relevant to each point in time.

Figure 11:
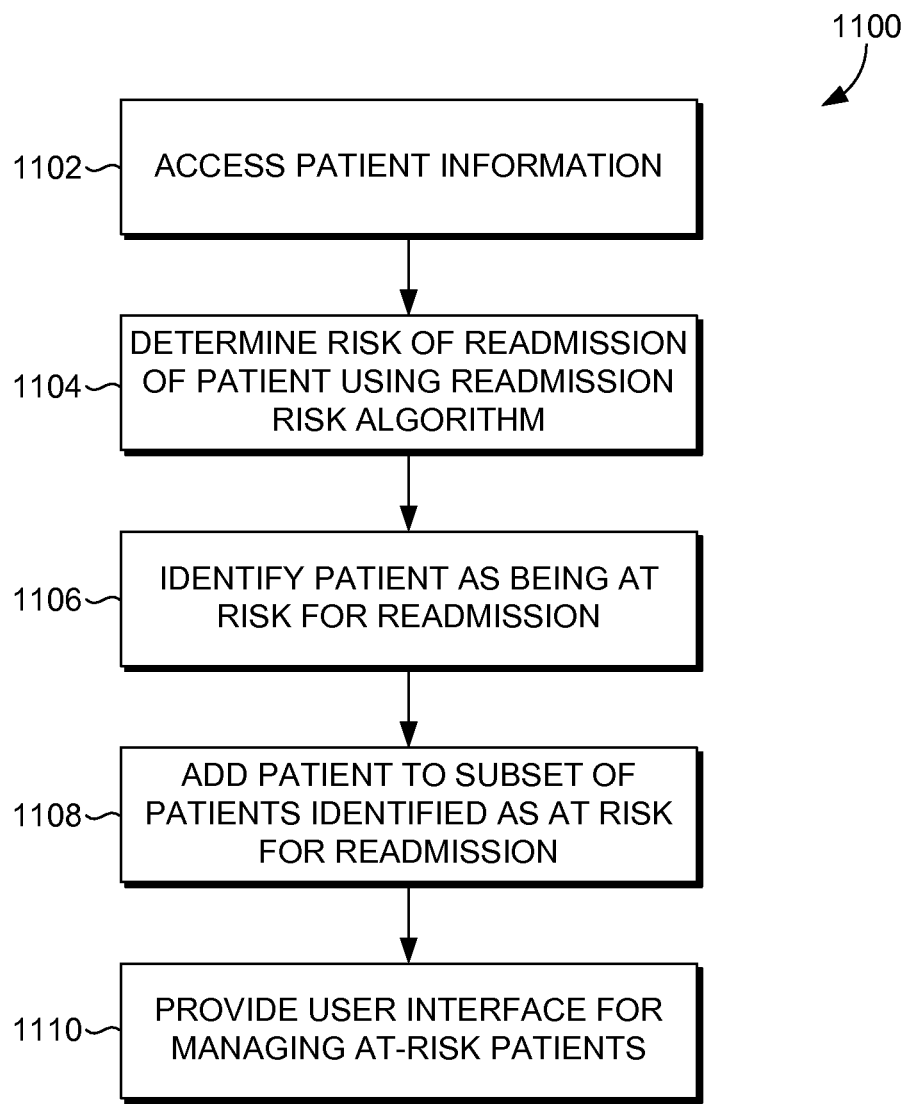
FIG. 11 is a flow diagram showing a method for assessing an individual patient's risk of readmission in accordance with an embodiment of the present invention.

Referring to FIG. 11, a flow diagram is provided that illustrates a method 1100 for assessing an individual patient's risk of readmission in accordance with an embodiment of the present invention. As shown at block 1102, patient information is accessed. As noted above, this may include accessing the patient information, for instance, from an electronic medical record, other medical data source, or by prompting a clinician to manually enter to information.

The patient information is used in conjunction with a readmission risk algorithm to determine the risk of readmission for the patient, as shown at block 1104. As previously discussed, the readmission risk algorithm is an algorithm that may be applied to patients of various conditions that are admitted to a healthcare facility. Based on the patient information and the readmission risk algorithm, the patient is identified as being at risk for readmission, as shown at block 1106. As such, the patient is added to a subset of patients identified as being at risk for readmission, as shown at block 1108. A user interface is generated and provided for presentation to a clinician or other user, as shown at block 1110. As previously discussed, the user interface may identify the various at-risk patients and assist in managing those patients.

Figure 12A:
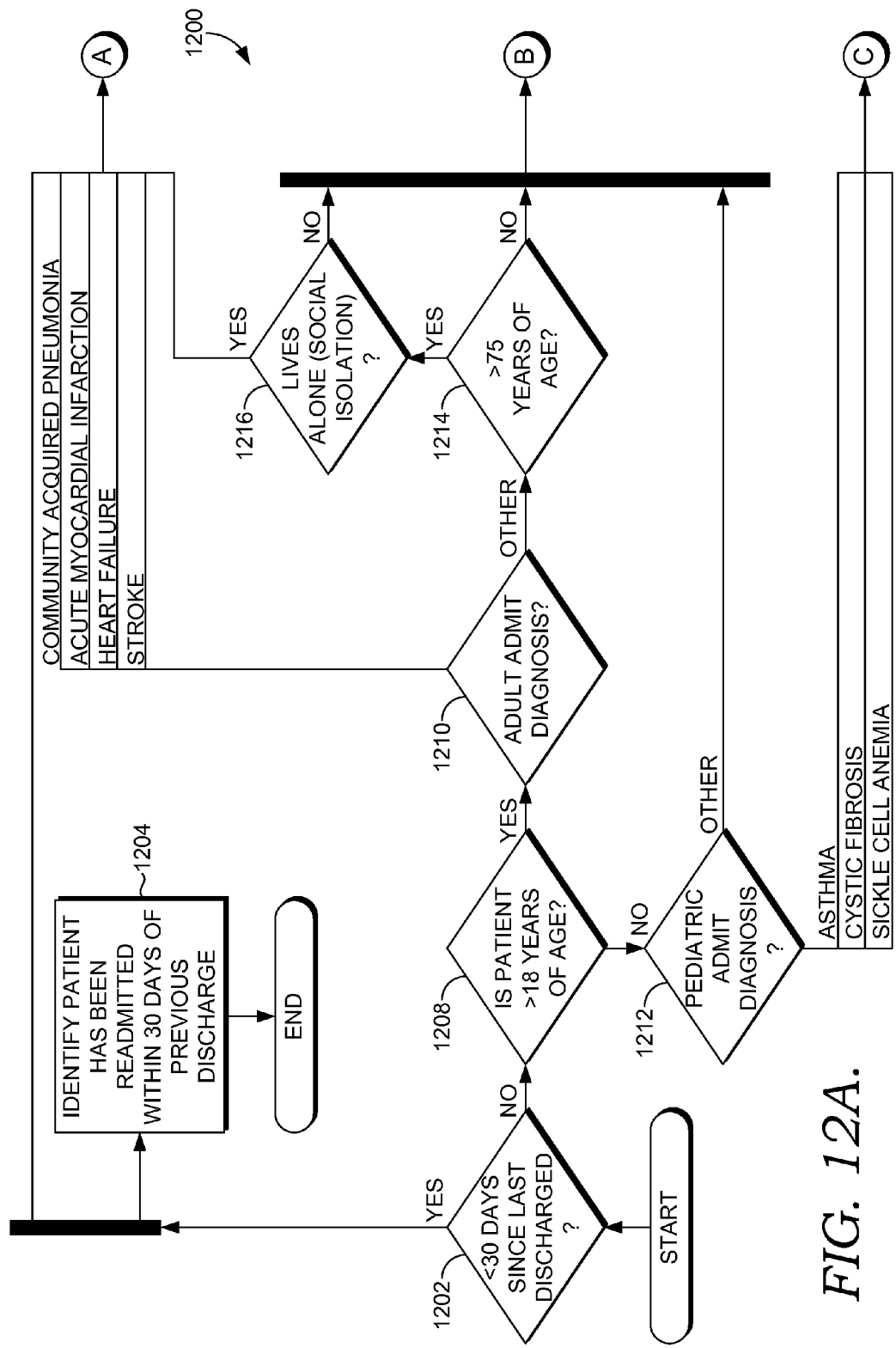
FIG. 12 is a flow diagram showing a method for employing an algorithm to determine the risk of readmission at the time of admission of a patient in accordance with an embodiment of the present invention.
Figure 12B:
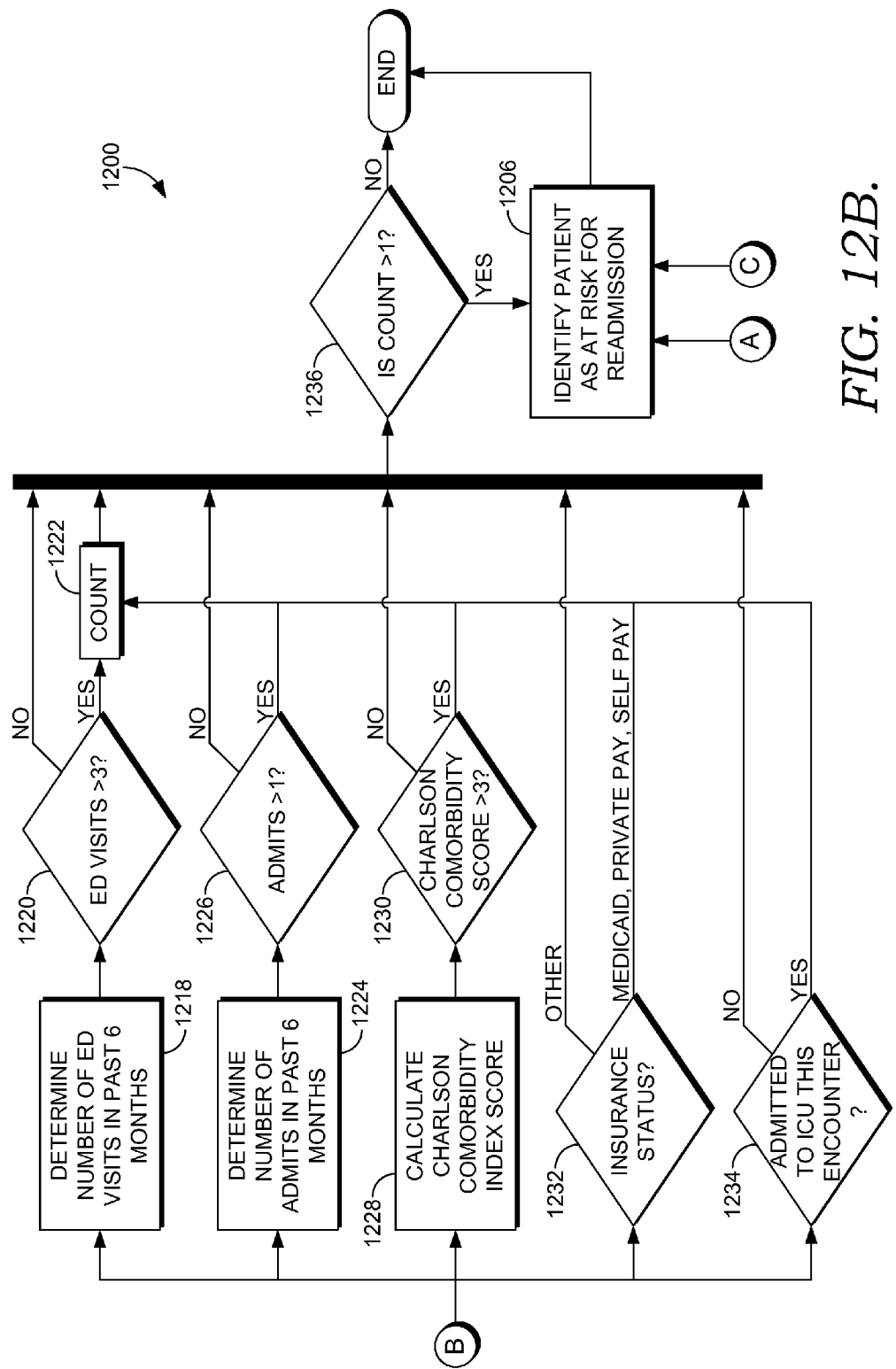
Figure 13:
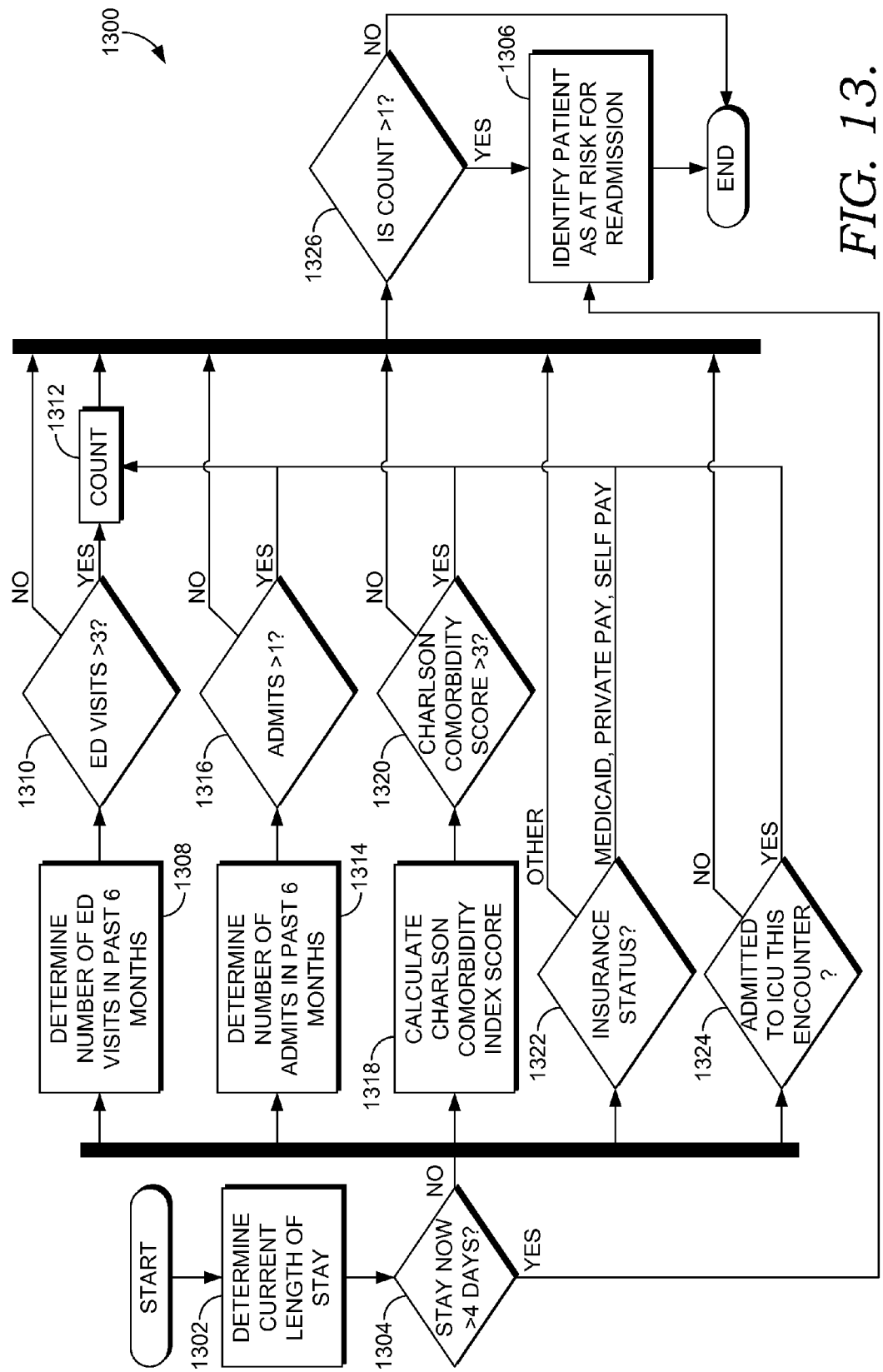
FIG. 13 is a flow diagram showing a method for employing an algorithm to determine the risk of readmission for a patient while the patient is admitted in accordance with an embodiment of the present invention.

Turning now to FIGS. 12 and 13, examples of specific algorithms that may be employed within some embodiments of the present invention are shown. It should be understood that these algorithms are provided by way of example only and not limitation. Other algorithms using other patient parameters may be employed within the scope of embodiments of the present invention.

With reference initially to FIG. 12, a flow diagram is provided that illustrates a method 1200 for employing an algorithm to determine the risk of readmission at the time of admission of a patient in accordance with an embodiment of the present invention. Generally, the purpose of this rule is to identify patients at risk for readmission that is evoked at time of a patient admission and may be run over all patients at admission. In accordance with this rule, a patient may automatically be flagged as a risk for readmission: if this encounter is a readmission within 30 days of a previous discharge; if the admission diagnosis is community-acquired pneumonia, acute myocardial infarction, heart failure, or stroke for patients over 18 years of age; if the admission diagnosis is asthma, cystic fibrosis, or sickle cell anemia for pediatric patients (e.g., patients under 18 years of age); or if the patient is greater than 75 years old and single or lives alone (social isolation). Additionally, a patient may automatically be flagged as a risk for readmission if any two of the following are true: the patient has had greater than three emergency room visits in the past 6 months; the patient has a Charlson Comorbidity Index score that is greater than 3; the patient has an insurance status of Medicaid, private pay, or self pay; or the patient has been admitted to the ICU during this encounter.

Initially, as shown at block 1202, a determination is made regarding whether the patient's last discharge date is less than 30 days since the current admission. If so, the patient is identified as being readmitted within 30 days of previous discharge at block 1204, and the patient is identified as a risk for readmission, as shown at block 1206. If the patient is not being readmitted within 30 days of a previous discharge, the age of the patient is determined at block 1208. If the patient is over 18 years of age, a determination is made at block 1210 regarding whether the patient has been diagnosed with community acquired pneumonia, acute myocardial infarction, heart failure or stroke. If the patient is diagnosed with one of those conditions, the patient is identified as a risk for readmission, as shown at block 1206. Alternatively, if the patient is less than 18 years of age (i.e., a pediatric patient), a determination is made at block 1212 regarding whether the patient has been diagnosed with asthma, cystic fibrosis, or sickle cell anemia. If the patient is diagnosed with one of those conditions, the patient is identified as a risk for readmission, as shown at block 1206. Although 18 years of age is used as a threshold age for the different diagnoses in the present embodiment, other embodiments may employ a different age. Additionally, other conditions may be used for identification of a patient as a risk for readmission beyond those identified above.

If the patient is not diagnosed with one of those conditions, the process continues by determining at block 1214 if the patient is over 75 years of age and determining at block 1216 if the patient is socially isolated (e.g., is single and/or lives alone). If the patient is both over 75 years of age and socially isolated, the patient is determined to be a risk for readmission at block 1206. If not, the process continues by determining if the patient meets two or more criteria such that the patient should be identified as a risk for readmission. As shown at block 1218, the number of emergency department (ED) visits for the patient in the past six months is determined. If it is determined at block 1220 that the number of ED visits is greater than three, the current criteria is satisfied and a counter is incremented at block 1222. Alternatively, if the number of visit does not exceed three, the current criteria is not satisfied and the counter is not incremented.

As shown at block 1224, the number of hospital admissions for the patient in the past six months is determined. If it is determined at block 1226 that the patient has more than one hospital admission in the past six months, the current criteria is satisfied and the counter is incremented at block 1222. Alternatively, if the patient has not had more than one hospital admission in the past six months, the current criteria is not satisfied and the counter is not incremented.

Next, a Charlson Comoribidity index score is calculated for the patient, as shown at block 1228. As is known in the art, the Charlson Comoribidity index is generated based on a number of comorbid conditions and traditionally used as a prediction of mortality outcomes for patients. If it is determined at block 1230 that the patient's Charlson Comoribidity index score is greater than three, the current criteria satisfied and the counter is incremented at block 1222. Alternatively, if the patient's Charlson Comoribidity index score is not greater than three, the current criteria is not satisfied and the counter is not incremented.

The insurance status of the patient is next identified at block 1232. If the patient's insurance status is Medicaid, private pay, or self pay, the current criteria is satisfied and the counter is incremented at block 1222. Alternatively, if the patient's insurance status is something else, the current criteria is not satisfied and the counter is not incremented.

A determination is made next at block 1234 regarding whether the patient will be admitted to the ICU during this encounter. If the patient will be admitted to the ICU during this encounter, the current criteria is satisfied and the counter is incremented at block 1222. Alternatively, if it is not currently planned to admit the patient to the ICU, the current criteria is not satisfied and the counter is not incremented.

After the different criteria has been evaluated, it is determined at block 1236 whether the counter exceeds one (i.e., two or more criteria have been met). If so, the patient is identified as a risk for readmission, as shown at block 1206. Alternatively, if the count does not exceed one, the patient is not identified as a risk for readmission, and the process ends.

Referring now to FIG. 13, a flow diagram is provided that illustrates a method 1300 for employing an algorithm to determine the risk of readmission for a patient while the patient is admitted in accordance with an embodiment of the present invention. The algorithm may be run daily or on some other schedule deemed appropriate by the healthcare facility. Generally, the purpose of this rule is to identify patients at risk for readmission while the patients are admitted at a hospital and may be run over all patients. In accordance with this rule, a patient may automatically be flagged as a risk for readmission if the patient's length of stay is now greater than four days. Additionally, a patient may automatically be flagged as a risk for readmission if any two of the following are true: the patient has had greater than three emergency room visits in the past 6 months; the patient has a Charlson Comorbidity Index score that is greater than 3; the patient has an insurance status of Medicaid, private pay, or self pay; or the patient has been admitted to the ICU during this encounter. Thus, the current algorithm for daily assessment of patients is similar to the algorithm employed at the time of admission discussed above with reference to FIG. 12 with some modifications.

Initially, as shown at block 1302, the patient's current length of stay is determined. A determination is made at block 1304 regarding whether the patient's length of stay is greater than four days. If the patient's length of stay is greater than four days, the patient is identified as a risk for readmission, as shown at block 1306. If the patient's length of stay is not greater than four days, the process continues by determining if the patient meets two or more criteria such that the patient should be identified as a risk for readmission. As shown at block 1308, the number of ED visits for the patient in the past six months is determined. If it is determined at block 1310 that the number of ED visits is greater than three, the current criteria is satisfied and a counter is incremented at block 1312. Alternatively, if the number of visit does not exceed three, the current criteria is not satisfied and the counter is not incremented.

As shown at block 1314, the number of hospital admissions for the patient in the past six months is determined. If it is determined at block 1316 that the patient has more than one hospital admission in the past six months, the current criteria is satisfied and the counter is incremented at block 1312. Alternatively, if the patient has not had more than one hospital admission in the past six months, the current criteria is not satisfied and the counter is not incremented.

Next, a Charlson Comoribidity index score is calculated for the patient, as shown at block 1318. If it is determined at block 1320 that the patient's Charlson Comorbidity index score is greater than three, the current criteria satisfied and the counter is incremented at block 1306. Alternatively, if the patient's Charlson Comorbidity index score is not greater than three, the current criteria is not satisfied and the counted is not incremented.

The insurance status of the patient is next identified at block 1322. If the patient's insurance status is Medicaid, private pay, or self pay, the current criteria is satisfied and the counter is incremented at block 1312. Alternatively, if the patient's insurance status is something else, the current criteria is not satisfied and the counter is not incremented.

A determination is made next at block 1324 regarding whether the patient will be admitted to the ICU during this encounter. If the patient will be admitted to the ICU during this encounter, the current criteria is satisfied and the counter is incremented at block 1312. Alternatively, if it is not currently planned to admit the patient to the ICU, the current criteria is not satisfied and the counter is not incremented.

After the different criteria has been evaluated, it is determined at block 1326 whether the counter exceeds one (i.e., two or more criteria have been met). If so, the patient is identified as a risk for readmission, as shown at block 1306. Alternatively, if the count does not exceed one, the patient is not identified as a risk for readmission, and the process ends.

As discussed previously, embodiments of the present invention include providing graphical user interfaces that facilitate management of patients at risk for readmission. FIGS. 14A through 14F are illustrative of user interfaces providing a readmission prevention worklist. It will be understood and appreciated by those of ordinary skill in the art that the screen displays of FIGS. 14A through 14F are provided by way of example only and are not intended to limit the scope of the present invention in any way.

Figure 14A:

Referring initially to FIG. 14A, an illustrative screen display is provided showing a readmission prevention worklist 1400 in accordance with an embodiment of the present invention. The readmission prevention worklist 1400 includes a list of patients and associated information to allow a clinician to manage patients at risk for readmission. The readmission worklist 1400 includes three tabs: an inpatient tab 1402 to display inpatients, a discharged tab 1404 to display patients that have been discharged, and a pre-admission tab 1406 to display patients at time of pre-admission. The inpatient tab 1402 is currently selected in FIG. 14A.

As shown in FIG. 14A, a variety of information is provided for listed patients. Initially, a patient information area 1408 is included to provide general patient information, such as the patient's name, age, and gender. Additionally, an admit diagnosis area 1410 is included to indicate the diagnosis for the patient at the time of admission.

The readmission prevention worklist 1400 also includes a support services area 1412, which provides information regarding whether different support services, such as social services and home health have been contacted on behalf of a patient and/or whether the services have been provided to the patient. By providing this information in the readmission prevention worklist 1400, a readmission preventionist or other clinician may view what support services are being provided for a patient and if appropriate, act on that information by, for instance, ensuring that appropriate support services are provided to the patient.

Next, the readmission prevention worklist 1400 includes a plan of care area 1414 that indicates a plan of care (or multiple plans of care) recommended for the patient based on determining the patient's risk for readmission. The plan of care may include various orders, consults, and/or tasks for patient care recommended to help reduce the risk of readmission for the patient. A clinician treating the patient may open the plan of care and initiate some or all components of the plan of care.

A disposition area 1416 is included to indicate where the patient is planning on going after discharge. Although a number of clinicians typically treat a patient to get the patient discharged, the clinicians often don't know where the patient is heading after discharge. The information, however, may be useful to a readmission preventionist or other clinician to help ensure that the patient receives the proper care and information dependent upon the patient's disposition after discharge to help reduce the risk that the patient will be readmitted.

A follow-up area 1418 and notes area 1420 are also included in the prevention worklist 1400. The follow-up area 1418 provides an indicated of whether a follow-up with a patient is needed and/or has occurred already. The notes area 1420 allows a readmission preventionist or other clinicians to track miscellaneous information regarding the patient and the patient's care relating to the patient's risk or readmission.

Figure 14B:

A user may access additional patient information within the readmission prevention worklist 1400. For instance, when a user selects an expand/collapse icon 1422 next to a patient, an additional patient information area 1424 is presented as shown in FIG. 14B. Among other things, the additional patient information includes a follow-up visit details area 1426 that lists historical information regarding previous follow-up visits scheduled for the patient. The information may include whether the patient made each scheduled visit, which may be useful to a readmission preventionist or other clinician in determining whether the patient is likely to make future follow-up visits when the patient is discharged. When follow-up visits have been missed, the clinician may investigate reasons why the visits were missed and attempt to find solutions to assist the patient in the future.

Figure 14C:
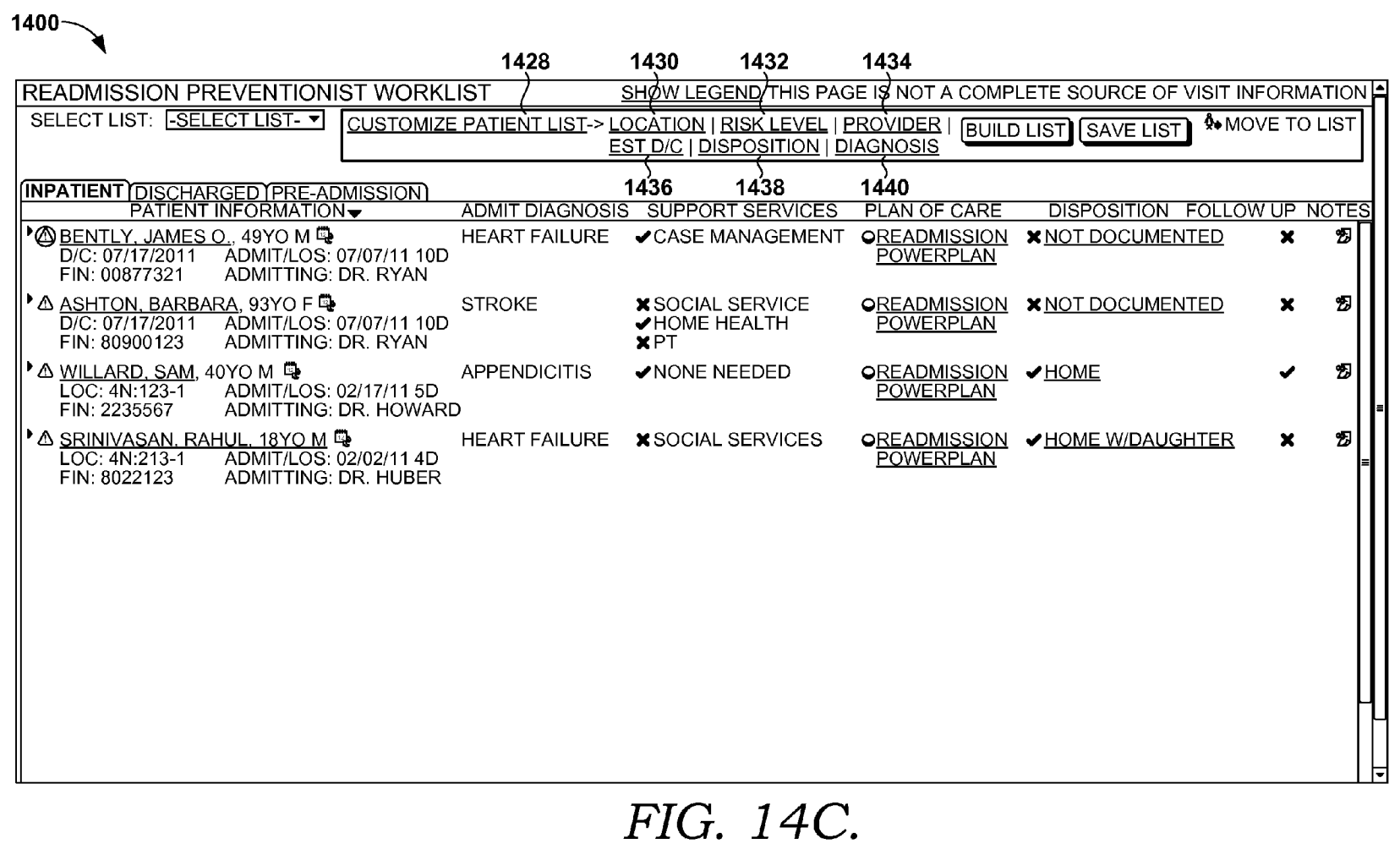

In some embodiments, the patients included in the readmission prevention worklist 1400 may be customized by the clinician. For instance, as shown in FIG. 14C, a customize patient list option 1428 is provided. When selected, areas for filtering the patients included in the list are provided as shown in FIG. 14C. The areas shown include filtering based on location 1430, readmission risk level 1432, provider 1434, estimated discharge date 1436, disposition 1438, and diagnosis 1440. It should be understood that the areas shown in FIG. 14C are provided by way of example only and other areas/criteria for filter patients may be employed.

Figure 14D:

A user may select an area and options within that area for filtering patients included in the list are provided. For instance, FIG. 14D illustrates when a user selects to filter based on readmission risk level 1432. As shown in FIG. 14D, a user may select to view all patients, low risk patients, high risk patients, and/or patients readmitted within 30 days of a previous discharge.

In some embodiments, such as that shown in FIG. 14A, an icon, such as the icon 1442, may be presented next to a patient to indicate that the patient has been determined to be at risk for readmission. When a user hovers over the icon 1442, information is provided regarding what criteria from the algorithm was met to identify the patient as at-risk for readmission. Generally, these may be viewed as identified risk factors for readmission for the patient. By way of illustration, FIG. 14E illustrates an information area 1444 that is presented when a user hovers over the icon 1442. The information area 1444 in the present example indicates that the criteria met for this patient that cause the patient to be identified as at-risk for readmission include a readmission within 30 days of a previous discharge and a diagnosis of hypertension for the patient.

As noted above, the readmission prevention worklist may be configured to include inpatients, discharged patients, and pre-admission patients on different tabs or other views. Turning to FIG. 14F, a view of the readmission prevention worklist 1400 is provided when the user selects the discharged tab 1404. The view is similar to that provided for inpatients with a few variations. For instance, a discharge diagnosis is provided instead of an admit diagnosis. Additionally, detailed follow-up information may be provided for the discharged patient to allow for tracking the discharged patient's follow-up visits and instigating actions if follow-visits are not being made by the discharged patient.

As can be understood, some embodiments of the present invention provide a readmission risk prediction model built using linear regression techniques and clinically relevant data. Some embodiments also provide inpatient treatment interventions and outpatient activity recommendations based on patients' monitored readmission risk. Further embodiments of the present invention are directed to applying a generic readmission risk algorithm to all patients admitted to a healthcare facility to identify those patients at greater risk for readmission and providing a readmission prevention worklist to manage those patients.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory computer storage media storing computer-useable instructions that, when used by one or more computing devices, cause the one or more computing devices to perform a method, the method comprising:
   accessing patient information for a first patient admitted or planned to be admitted to a healthcare facility;
   determining, based on the patient information, if each of a first set of risk factors is satisfied, the first set of risk factors including:
   (1) the first patient is being admitted within 30 days from a previous admission,
   (2) the first patient is diagnosed with one of a plurality of predetermined conditions,
   (3) the first patient's age is above a threshold age and the patient lives in social isolation, and
   (4) the first patient has a length of stay at the healthcare facility greater than a threshold length of stay;
   determining, based on the patient information, if each of a second set of risk factors is satisfied, the second set of risk factors including:
   (1) a number of emergency department visits for the first patient over a given time period exceeds a threshold number of emergency department visits,
   (2) a number of admissions for the first patient over a given time period exceeds a threshold number of admissions,
   (3) a comorbidity score for the first patient exceeds a comorbidity score threshold,
   (4) the first patient has a predetermined type of insurance, and
   (5) the first patient is being admitted to the intensive care unit;
   determining if at least one risk factor from the first set of risk factors has been satisfied or at least two risk factors from the second set of risk factors have been satisfied;
   if no risk factor from the first set of risk factors has been satisfied and no more than one risk factor from the second set of risk factors has been satisfied, identifying the first patent as not being at risk for readmission; and
   if at least one risk factor from the first set of risk factors has been satisfied or if at least two risk factors from the second set of risk factors has been satisfied, identifying the first patient as being at risk for readmission and including the first patient in a user interface for presentation that facilitates managing a plurality of patients identified as being at risk for readmission.

2. The one or more computer storage media of claim 1, wherein the method further comprises suggesting a readmission prevention plan of care for the first patient based on identifying the patient as being at risk for readmission.

3. The one or more computer storage media of claim 1, wherein the user interface provides an indication regarding one or more risk factors causing the first patient to be identified as being at risk for readmission.

4. The one or more computer storage media of claim 1, wherein the first patient is identified as being at risk for readmission at a time of admission of the first patient.

5. The one or more computer storage media of claim 1, wherein the first patient is identified as being at risk for readmission while the first patient is admitted at the healthcare facility.

6. The one or more computer storage media of claim 1, wherein the first patient is identified as being at risk for readmission prior to discharging the first patient from the healthcare facility.

7. The one or more computer storage media of claim 1, wherein the first patient is identified as being at risk for readmission after discharging the first patient from the healthcare facility.

8. A method comprising:
    accessing, by a first computing process, patient information for a first patient admitted or planned to be admitted to a healthcare facility;
    determining, by a second computing process, based on the patient information, if each of a first set of risk factors is satisfied, the first set of risk factors including:
        (1) the first patient is being admitted within 30 days from a previous admission,
        (2) the first patient is diagnosed with one of a plurality of predetermined conditions,
        (3) the first patient's age is above a threshold age and the patient lives in social isolation, and
        (4) the first patient has a length of stay at the healthcare facility greater than a threshold length of stay;
    determining, by a third computing process, based on the patient information, if each of a second set of risk factors is satisfied, the second set of risk factors including:
        (1) a number of emergency department visits for the first patient over a given time period exceeds a threshold number of emergency department visits,
        (2) a number of admissions for the first patient over a given time period exceeds a threshold number of admissions,
        (3) a comorbidity score for the first patient exceeds a comorbidity score threshold,
        (4) the first patient has a predetermined type of insurance, and
        (5) the first patient is being admitted to the intensive care unit;
    determining, by a fourth computing process, if at least one risk factor from the first set of risk factors has been satisfied or at least two risk factors from the second set of risk factors have been satisfied;
    if no risk factor from the first set of risk factors has been satisfied and no more than one risk factor from the second set of risk factors has been satisfied, identifying, by a fifth computing process, the first patent as not being at risk for readmission; and
    if at least one risk factor from the first set of risk factors has been satisfied or if at least two risk factors from the second set of risk factors has been satisfied, identifying, by a sixth computing process, the first patient as being at risk for readmission and including the first patient in a user interface for presentation that facilitates managing a plurality of patients identified as being at risk for readmission;
    wherein the computing processes are performed by one or more computing devices.

9. The method of claim 8, wherein the method further comprises suggesting a readmission prevention plan of care for the first patient based on identifying the patient as being at risk for readmission.

10. The method of claim 8, wherein the user interface provides an indication regarding one or more risk factors causing the first patient to be identified as being at risk for readmission.

11. The method of claim 8, wherein the first patient is identified as being at risk for readmission at a time of admission of the first patient.

12. The method of claim 8, wherein the first patient is identified as being at risk for readmission while the first patient is admitted at the healthcare facility.

13. The method of claim 8, wherein the first patient is identified as being at risk for readmission prior to discharging the first patient from the healthcare facility.

14. The method of claim 8, wherein the first patient is identified as being at risk for readmission after discharging the first patient from the healthcare facility.

15. A computerized system comprising:
    one or more processors; and
    one or more computer storage media storing computer-useable instructions that, when used by the one or more processors, cause the one or more processors to:
    access patient information for a first patient admitted or planned to be admitted to a healthcare facility;
    determine, based on the patient information, if each of a first set of risk factors is satisfied, the first set of risk factors including:
        (1) the first patient is being admitted within 30 days from a previous admission,
        (2) the first patient is diagnosed with one of a plurality of predetermined conditions,
        (3) the first patient's age is above a threshold age and the patient lives in social isolation, and
        (4) the first patient has a length of stay at the healthcare facility greater than a threshold length of stay;
    determine, based on the patient information, if each of a second set of risk factors is satisfied, the second set of risk factors including:
        (1) a number of emergency department visits for the first patient over a given time period exceeds a threshold number of emergency department visits,
        (2) a number of admissions for the first patient over a given time period exceeds a threshold number of admissions,
        (3) a comorbidity score for the first patient exceeds a comorbidity score threshold,
        (4) the first patient has a predetermined type of insurance, and
        (5) the first patient is being admitted to the intensive care unit;
    determine if at least one risk factor from the first set of risk factors has been satisfied or at least two risk factors from the second set of risk factors have been satisfied;
    if no risk factor from the first set of risk factors has been satisfied and no more than one risk factor from the second set of risk factors has been satisfied, identify the first patent as not being at risk for readmission; and
    if at least one risk factor from the first set of risk factors has been satisfied or if at least two risk factors from the second set of risk factors has been satisfied, identify the first patient as being at risk for readmission and include the first patient in a user interface for presentation that facilitates managing a plurality of patients identified as being at risk for readmission.

16. The computerized system of claim 15, wherein the computer-useable instructions further cause the one or more processors to suggest a readmission prevention plan of care for the first patient based on identifying the patient as being at risk for readmission.

17. The computerized system of claim 15, wherein the user interface provides an indication regarding one or more risk factors causing the first patient to be identified as being at risk for readmission.

18. The computerized system of claim 15, wherein the first patient as identified as being at risk for readmission at a time selected from the following: a time of admission of the first patient; while the first patient is admitted at the healthcare facility; prior to discharging the first patient from the healthcare facility; and after discharging the first patient from the healthcare facility.

* * * * *